US009506907B2

(12) United States Patent
Bergkvist et al.

(10) Patent No.: US 9,506,907 B2
(45) Date of Patent: Nov. 29, 2016

(54) BIOENGINEERED HUMAN TRABECULAR MESHWORK FOR BIOLOGICAL APPLICATIONS

(71) Applicant: The Research Foundation of State University of New York, Albany, NY (US)

(72) Inventors: Magnus Bergkvist, Albany, NY (US); Sara Brenner, Voorheesville, NY (US); Ioannis Danias, Staten Island, NY (US); Susan Sharfstein, Niskayuna, NY (US); Yubing Xie, Cohoes, NY (US); Alison Gracias, Albany, NY (US); Karen Y. Torrejon, Albany, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 13/771,007

(22) Filed: Feb. 19, 2013

(65) Prior Publication Data
US 2014/0038221 A1    Feb. 6, 2014

Related U.S. Application Data

(60) Provisional application No. 61/600,988, filed on Feb. 20, 2012.

(51) Int. Cl.
| | |
|---|---|
| *C12Q 1/02* | (2006.01) |
| *G01N 33/483* | (2006.01) |
| *C12N 5/079* | (2010.01) |
| *A61F 9/007* | (2006.01) |

(52) U.S. Cl.
CPC ......... *G01N 33/4833* (2013.01); *C12N 5/0621* (2013.01); *A61F 9/00781* (2013.01); *C12N 2503/02* (2013.01); *C12N 2513/00* (2013.01); *C12N 2533/30* (2013.01); *C12N 2533/32* (2013.01); *C12N 2533/54* (2013.01)

(58) Field of Classification Search
CPC .................... A61F 9/00781; C12N 5/0621
USPC ................ 435/287.5, 402; 3/287.5
See application file for complete search history.

(56) References Cited

U.S. PATENT DOCUMENTS

2010/0119711 A1    5/2010    Cady et al.

OTHER PUBLICATIONS

Peters, Donna M., Building and artificial trabecular meshwork. NIH Research Portfolio Online Reporting Tools (RePORT) [online]. Sep. 7, 2007 [retrieved Jul. 14, 2014]. Retrieved from the Internet <URL: http://projectreporter.nih.gov/project_info_details.cfm?aid=7280329&icde=0>.*
Hennemeyer et al., Cell proliferation assays on plasma activated SU-8. Microelectronic Engineering, vol. 85 (2008) pp. 1298-1302.*
Tao et al., Off-wafer fabrication and surface modification of asymmetric 3D SU-8 microparticles. Nature Protocols, vol. 1, No. 6 (2006) p. 3153-3158).*
Tamm, Ernst., (The trabecular meshwork outflow pathways: structural and functional aspects. Experimental Eye Research, vol. 88 (2009) pp. 648-655.*
Buller and Johnson, Segmental variability of the trabecular meshwork in normal and glaucomatous eyes. Opthamology & Visual Science. vol. 35, No. 11 (Oct. 1994) pp. 3841-3851.*
Bahler, Cindy K. et al., "Trabecular Bypass Stents Decrease Intraocular Pressure in Cultured Human Anterior Segments," 2004 American Journal of Opthhalmology, vol. 138, No. 6, pp. 988-994.
Bahler, Cindy K. et al., "Second-generation Trabecular Meshwork Bypass Stent (iStent inject) Increases Outflow Facility in Cultured Human Anterior Segments," 2012 American Journal of Ophthalmology, vol. 153, No. 6, pp. 1206-1213.
Bogdanov, A.L. et al., "Use of SU-8 photoresist for very high aspect ratio x-ray lithography," 2000 Microelectronic Engineering, vol. 53, pp. 493-496.
Helies, P. et al., "Le trabeculum artificiel (MESH)," 1998 English Abstract, J. Fr. Ophtalmol, vol. 21, No. 5, pp. 351-360.
Mata, Alvaro et al., "Fabrication of multi-layer SU-8 microstructures," 2006 J. Micromech. Microeng. vol. 16, pp. 276-284.
Mata, Alvaro et al., "A three-dimensional scaffold with precise micro-architecture and surface micro-textures," 2009 Biomaterials, vol. 30, pp. 4610-4617.
Minckler, Don S. et al., "Use of novel devices for control of intraocular pressure," 2009 Experimental Eye Research, vol. 88, pp. 792-798.
Padgen, Michael R. et al., "SU-8 Microfluidic Channels with Porous Sidewalls for Biological Applications," 2009 Proc of SPIE vol. 7207, pp. 720707-1-720707-8.
Pan, Tingrui et al., "An Artificial Nano-Drainage Implant (ANDI) for Glaucoma Treatment," 2006 Proceedings of the 28th IEEE, EMBS Annual International Conference, New York City, US, pp. 3174-3177.
Perkins, Todd W. et al., "Trabecular Meshwork Cells Grown on Filters: Conductivity and Cyrochalasin Effects," 1988 Investigative Ophthalmology & Visual Science, vol. 29, No. 12, pp. 1836-1846.
Polansky, Jon R. et al., "Trabecular Meshwork Cell Culture in Glaucoma Research: Evaluation of Biological Activity and Structural Properties of Human Trabecular Cells in Vitro," 1984 Ophthalmology, vol. 91 No. 6, pp. 580-595.
Russell, Paul et al., "Response of Human Trabecular Meshwork Cells to Topographic Cues on the Nanoscale Level," 2008 Investigative Ophthalmology & Visual Science, vol. 49, No. 2, pp. 629-635.

(Continued)

*Primary Examiner* — Kara Johnson
(74) *Attorney, Agent, or Firm* — Harris Beach PLLC

(57) ABSTRACT

The present invention relates to methods of manufacture and utility of an artificial trabecular meshwork [TM] that utilizes micro- and nanofabricated materials bioengineered to mimic the structure and function of native outflow system of the eye.

19 Claims, 16 Drawing Sheets

(56) References Cited

OTHER PUBLICATIONS

Vickerman V. et al., "Direct Imaging of Giant Vacuole Dynamics of Schlemm's Canal Endothelial Cells Using a Novel in vitro Microfluidics-Based 3D Cell Culture System," 2010 Invest. Ophthalmol. Vis Sci, vol. 51, E-Abstract 5834 (2 pages).

Wood, Joshua A. et al., "Substratum Compliance Regulates Human Trabecular Meshwork Cell Behaviors and Response to Latrunculin B," 2011 Investigative Ophthalmology & VisualScience, vol. 52, No. 13, pp. 9298-9303.

Peters, Donna, 2006-2008, Progress reports RO3EY16236-02, -03 and Final Report awarded to Donna Peters by the National Eye Institute (NEI).

Kim, Bongsu, "Multidisciplinary Engineered Approaches to Investigate Human Trabecular Meshwork Endothelial Cells in Regulation of Intraocular Pressure," 2011 Dissertation, Ohio State University, Graduate Program in Biomedical Engineering.

* cited by examiner

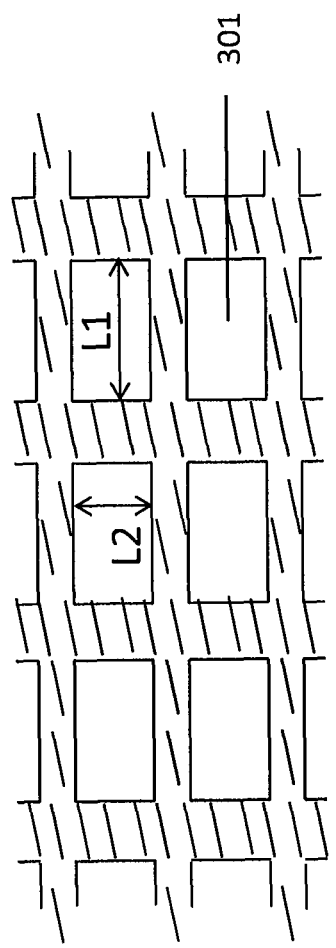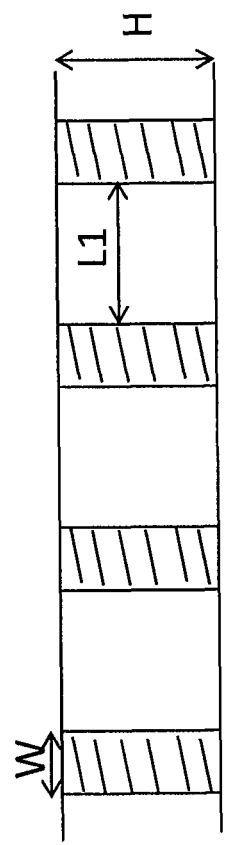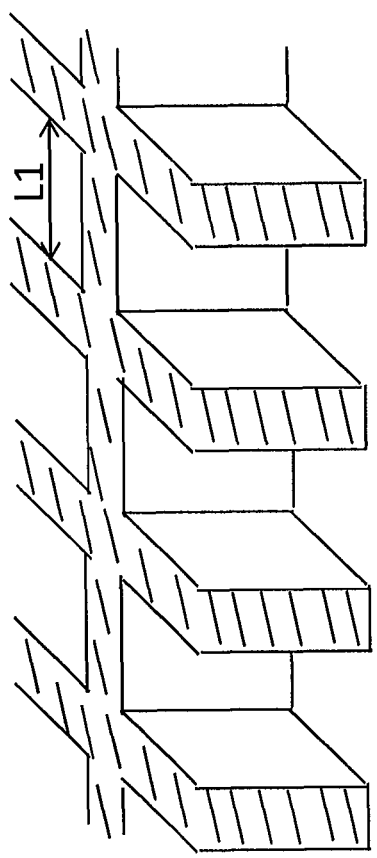
FIG 3A
FIG 3B
FIG 3C

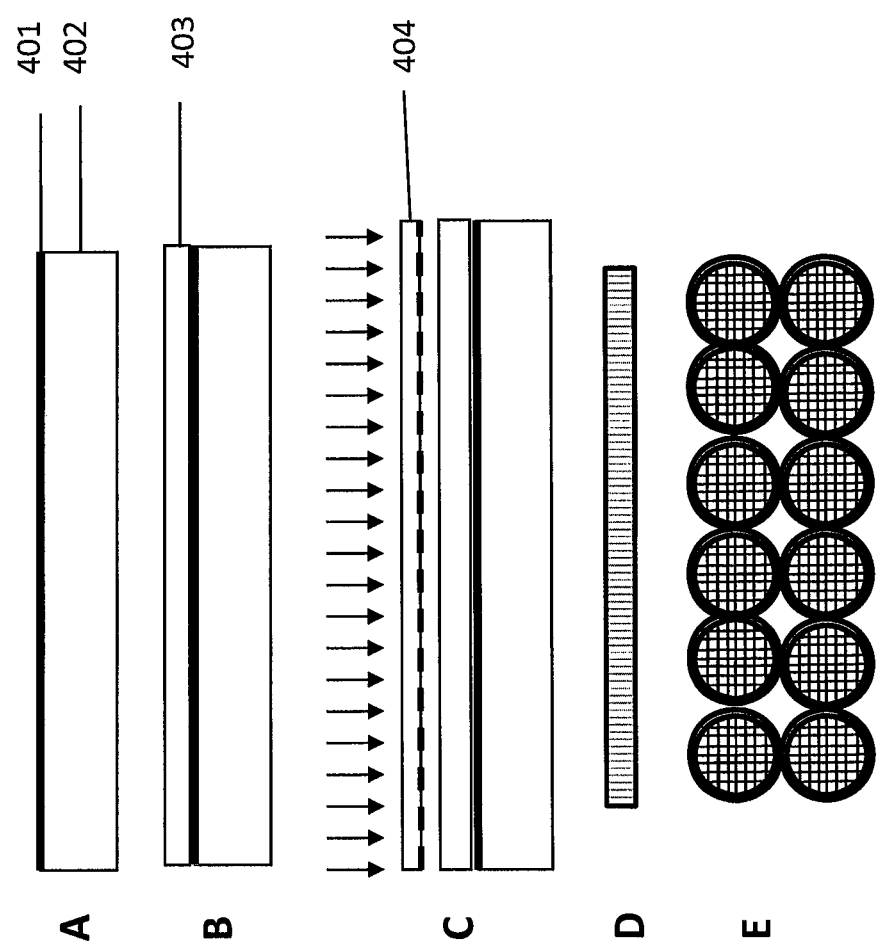

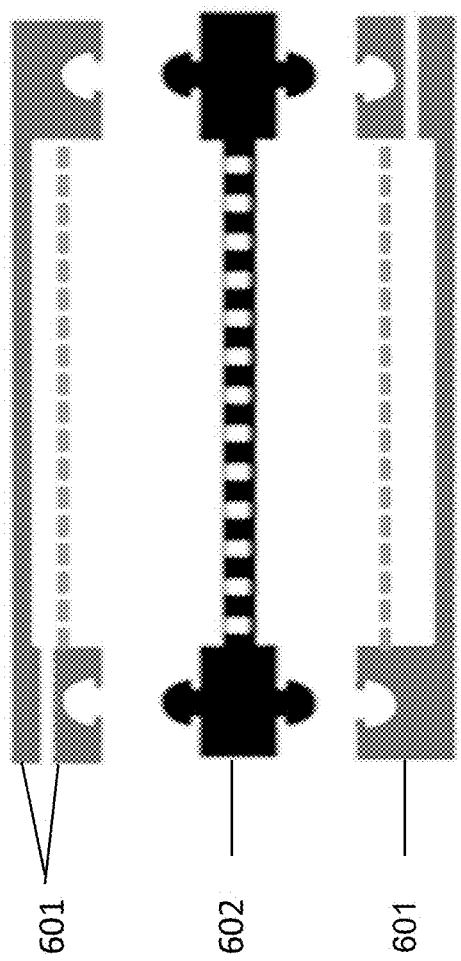
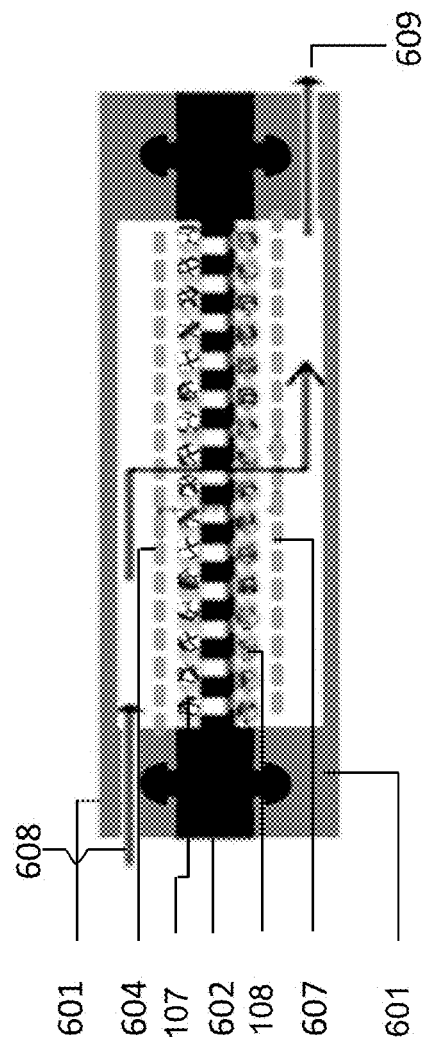
FIG 6A
FIG 6B

BIOENGINEERED HUMAN TRABECULAR MESHWORK FOR BIOLOGICAL APPLICATIONS

CROSS REFERENCE TO RELATED APPLICATIONS

This application claims priority to U.S. Provisional Patent Application Ser. No. 61/600,988 filed on Feb. 20, 2012, the entire contents of which are incorporated herein by reference.

FIELD OF STUDY

This invention is in the field of bioengineering. More particularly, the present invention is directed to bioengineering complex 3-dimensional (3-D) micro- and nanostructured scaffolds which after appropriate modifications are seeded with multiple live human, animal or bioengineered cells to produce functional units that closely resemble the physiology of the outflow pathways of the eye. Particular embodiments involve configurations that can be used with a 3-D cell culture chamber for high-throughput screening of medications for their effect on intraocular pressure (IOP) as well as configurations that can be used as therapeutic devices in glaucoma.

BRIEF DESCRIPTION OF THE BACKGROUND OF THE INVENTION

The field of bioengineering combines the methods of engineering with the principles of life science to understand the structural and functional relationships in normal and pathological organs. A goal of bioengineering is also the development and ultimate application of biological substitutes to restore, maintain, and improve organ functions, and thus, improve quality of life.

The eye is the organ of vision. A space called the anterior chamber is located in the front part of the eye. It is filled with a clear, watery fluid called aqueous humor. This fluid is continuously produced inside the eye by the ciliary body. It is different from tears, which are produced by glands outside of the eye and moisten the outer surface of the eyeball. This intraocular fluid flows out through the pupil, into the anterior chamber and exits the chamber at the angle where the iris and cornea meet. The majority of this fluid in humans flows through a structure called the trabecular meshwork (TM) into a channel called Schlemm's canal (SC). It then flows into 8-13 collector channels, which communicate with the venous system, thus eventually being absorbed into the bloodstream.

The human trabecular meshwork (HTM) is a spongy meshwork of drainage canals composed of collagenous and elastin extracellular matrix (ECM) on which reside cells specialized in the production and maintenance of this matrix, phagocytosis of debris, and regulation of aqueous humor flow. Cells in the wall of SC that is adjacent to the HTM also provide resistance to this flow. Proper drainage keeps the eye pressure at a normal level. The production, flow, and drainage of this intraocular fluid is an active continuous process that is needed for the health of the eye.

The inner pressure of the eye (intraocular pressure, IOP) depends on the rate of elimination of aqueous humor mostly through the HTM as the rate of production is relatively constant. If the eye's drainage system is working optimally, then any rise in IOP is prevented since the aqueous humor can drain out into the bloodstream. While IOP can vary at different times of the day, it is maintained within a narrow optimal range for normal individuals.

When resistance to outflow of aqueous humor rises because of disease, trauma to the HTM, or certain pharmacologic treatments, IOP increases above the normal range. High pressure may damage the sensitive optic nerve and result in vision loss. This condition is called glaucoma. In the majority of cases of open angle glaucoma, the eye's TM drainage system becomes "clogged" so the aqueous humor cannot drain efficiently. As aqueous outflow is impeded, IOP rises within the eye.

The eye has approximately one million nerve fibers that originate in the retina and form the optic nerve. These nerve fibers meet at the optic disc. As IOP builds up within the eye, it damages the nerve fibers and they begin to die. As the nerve fibers die, the optic disc begins to hollow and develops a cupped or curved shape. If the IOP remains too high for an individual, for too long, then it could lead to optic nerve damage and result in vision loss.

The most recent statistics by the World Health Organization have placed glaucoma as a leading cause of irreversible blindness worldwide, affecting nearly 70 million people. In addition, with the world's population aging, it is expected that the number of people affected by glaucoma will increase dramatically. Currently, the only treatment for glaucoma is lowering IOP, which is the only modifiable risk factor for glaucoma.

The HTM is an intricate 3-D structure, consisting of HTM cells and their associated ECM, including interwoven collagen beams and perforated sheets composed of elastin arranged in a laminar pattern. Glaucoma is thus linked to HTM structure and function where structural changes of the HTM likely affect tissue rigidity and biomechanical properties that influence its resistance to flow.

Current treatments of glaucoma involve lowering the IOP by means of decreasing aqueous humor production or increasing non-trabecular aqueous humor outflow. Few therapeutic agents primarily target the HTM. Of those few, in current clinical practice, only miotics (i.e. direct and indirect cholinergic agonists, e.g., pilocarpine) increase HTM outflow by contracting the ciliary muscle, the tendons of which "stretch" the TM to increase flow. The compound: latruncunlin-B (Lat-B), has recently gained interest as a potential novel glaucoma treatment. Lat-B increases aqueous humor outflow and decreases IOP by directly acting on HTM cells. Further advances in pharmacological treatment of glaucoma are currently limited by the lack of proper, efficient, in vitro models for the screening of new potential therapeutics.

While conventional HTM cell cultures may be useful for studying the biology of HTM cells, they are not suitable for evaluating the effects of medications on outflow facility (see, e.g., Koga et al., Exp Eye Res 82:362-70, 2006. Current outflow facility studies mainly rely on anterior segments of animal or human eyes (see, e.g., Ethier et al., Invest Ophthalmol Vis Sci 47:1991-8, 2006; however, the preparation of these perfusion systems is cumbersome, expensive, and not suitable for high-throughput screening. Therefore, there is a great need for a bioengineered, functional, in vitro HTM model for glaucoma drug screening.

Commercially available, porous membranes were tried for HTM cell culture, but with limited success (see, e.g., Perkin et al., Invest Ophthalmol Vis Sci 29:1836-1846, 1988). This is because these membranes either possess irregular pore structure or low porosity (e.g., 4-20%), which limits their performance for HTM cell growth and usefulness in perfusion experiments. In addition these membranes have not been adapted, suggested or used for high-throughput screening of medications. There is a need to overcome these disadvantages with an in vitro system that offers a new avenue for understanding the HTM physiology at the molecular and cellular level and testing pharmacological agents that affect trabecular outflow facility in humans. Recently, such a system was proposed to culture SC cells in a microfluidics-based hydrogel culture system that can be used to study the formation of giant vacuoles in SC cells (see, e.g., Vickerman et al., Invest Ophthalmol Vis Sci 51:E-Abstract, 5834, 2010). However, this system does not contain HTM cells, has not been used for study of pharmacologic agents, and would be difficult and very expensive to integrate in a high throughput system. In particular, a hydrogel-based system is not ideal for regulating flow and studying flow physiology at a stable condition.

Surgical glaucoma treatment attempts to either "stimulate" the TM to work better (laser trabeculoplasty) or altogether bypasses the TM, shunting the aqueous humor mostly to an extraocular space. Incisional glaucoma surgery currently consists of either trabeculectomy or seton surgery.

Trabeculectomy creates a fistula from the anterior chamber to the anterior subtenon's space. There aqueous humor is sequestered in cystic spaces and either gets absorbed in lymphatic vessels, enters episcleral veins or transudates through the conjunctiva. Trabeculectomy success depends in large part on appropriate management of the fibrotic (healing) response of each individual patient. Since this response is variable, surgical outcomes are often unpredictable. Even in cases where trabeculectomy is initially deemed successful, aqueous flow into the subtenon's space leads to progressive remodeling of the periocular and episcleral tissues. This remodeling ultimately leads to failure of surgery by limiting the area of diffusion of the aqueous thus increasing resistance to flow.

Seton surgery utilizes a prosthetic conduit (a silicone tube) to shunt aqueous humor to the posterior (>8 mm from the limbus) subtenon's space. The aqueous diffuses over the area of a variably sized plate that is attached to the tube. A fibrous capsule is formed by the host over the plate. The permeability of this capsule determines the rate of aqueous diffusion. Tube surgery is equally effective to trabeculectomy (see, e.g., Gedde et al., Curr Opin Ophthalmol 23:118-26, 2012). Its long-term failure is again the result of tissue remodeling of the plate capsule to make it progressively thicker and less permeable.

It is thus obvious that incisional glaucoma surgery is in a strict sense "non-physiologic". Ideally, such surgery would bypass the defective/diseased TM/SC complex but would utilize the downstream physiological outflow path (SC, aqueous veins). Attempts to create such bypass with zero resistance to flow have in the long-term generally been unsuccessful to date. In the short term, they provide only small IOP decreases (see, e.g., Morales-Fernandez et al., Eur J Ophthalmol 22:670-3, 2012). In addition, since such attempts rely on complete bypass of the TM/SC complex, they can cause early hypotony, which can lead to significant vision-threatening complications. In addition, if the surgery is effective, the regulatory function of the TM/SC complex is lost.

Prior attempts to create a device that would utilize acellular micropatterned structures (see, e.g., Helies et al., J Fr Ophtalmol 21:351-60, 1998; Pan et al., Proc 28th IEEE EMBS Ann Int Conf, 2006) to act as HTM have failed to result in clinically useful devices because they rely on passive regulation of flow afforded by very narrow channels that over time get occluded by cells and debris in the aqueous humor in vivo, as well as by the fact that as with conventional glaucoma surgery, they shunt aqueous humor to the subconjunctival space, thus inducing a fibrotic response.

Thus the development of a bioengineered HTM that can replace the defective HTM in glaucoma would provide a novel and highly desirable way of understanding and treating the disease.

SUMMARY

An aspect of the present invention is a method of bioengineering a trabecular meshwork [HTM] comprising: providing a wafer with a upper surface; applying a release layer to said upper surface of said wafer, yielding a top surface; layering on said top surface a substrate conducive for a HTM cell source to yield a 3-D trabecular meshwork [TM]; constructing a 3-D micro- and nanostructured scaffold from said substrate by optimizing at least a property of said substrate to yield a 3-D trabecular meshwork [TM]; releasing said 3-D micro- and nanostructured scaffold from said top surface; coating said 3-D micro- and nanostructured scaffold with a HTM biocompatible coating providing optimal attachment of HTM cells; sterilizing said 3-D micro- and nanopatterned scaffold coated with said HTM biocompatible coating; seeding thereafter a pre-determined cell seeding density of the HTM cells on said coated said scaffold; culturing a trabecular meshwork of the HTM cells on the substrate for at least enough days to permit forming of at least a monolayer horizontally of the HTM cells that are sending cellular processes vertically and forming said HTM cell to said HTM cell adhesions; allowing thus for said HTM cells to form a confluent trabecular meshwork; and yielding a TM that mimics the perforated sheet-like structure and outflow characteristics and physiological function of TM found in vivo with utility in screening and therapy of HTM outflow facility.

Another aspect of the invention is a method of bioengineering the HTM, comprising optimizing the geometry of the micro- and nanofabricated scaffolds to include a pore with a first measurement (L1) and a second measurement (L2); a set of four walls defining a three-dimensional shape of said pore, the set of four walls having a beam width (W) and a beam height (H); allowing for HTM cells to grow into a confluent layer by said first measurement of the pore (L1), and said second measurement of the pore (L2), being smaller than a HTM cell; facilitating a vertical direction of the HTM cells to send out cellular processes, by pre-determining the beam width (W) and said beam height (H); and facilitating subsequently, the formation of the three dimensional porous trabecular meshwork that mimics the in vivo HTM.

Another aspect of the invention is a bioengineered trabecular meshwork [HTM] comprising: a micro- and nanofabricated scaffolds including a pore with a first measurement (L1) and a second measurement (L2); a set of four walls defining a three-dimensional shape of the said pore, the set of four walls having a beam width (W) and a beam height (H); said first measurement of the pore (L1), and said second measurement of the pore (L2), being smaller than a HTM cell, allowing for HTM cells to grow into a confluent layer; while the beam width (W) and said beam height (H) are facilitating vertical direction of the HTM cells to send out cellular processes, and thus, forming a three dimensional porous trabecular meshwork that mimics the porosity of an in vivo HTM.

Another aspect of the invention is a high-throughput screening artificial HTM screening system comprising: a perfusion chamber providing a housing with a controlled environment chamber maintained at a constant temperature and flow rate, with the ability to maintain a constant flow rate conducive for HTM cells cultures at about at least 1 ul/min to study the experimental effects on the artificial HTM in a scaffold holder; a multi-channel perfusion array including a substrate holder with, a first element including a multi-well, microtiter plate designed as an insert to hold the 3-D micro- and nanostructured scaffolds, wherein said scaffolds are prevented from touching the base of said insert by using a fourth element, having the ability of achieving the function of separating the first element from said scaffold; a second element including a bottom array plate designed to collect effluents; and a third element including a top array plate designed to allow entry of perfusion media in a sealed manner; with the first element sandwiched between the second element and the third element; a pressure transducer for pressure and flow measurement, communicating with the substrate holder, having the ability to maintain a constant flow rate that is conducive for the HTM cells growth, and proliferation at levels that provide an ability to study the effect of flow rate changes on the artificial HTM; a monitor having the ability to measure and monitor at least the constant flow rate and communicating with at least the pressure transducer; a perfusion media entry system communicating with the pressure transducer; an experimental agent media entry system communicating with the pressure transducer; and providing an in vitro model for aqueous outflow facility screening.

A still further aspect of the present invention is an artificial TM clinical device comprising: an assembled housing, wherein there is contained a perfusion area; a first element of a cell support structure (FIG. 6; 602, FIG. 7; 602); a second element of a safety filters (FIG. 6; 604); a third element of a bottom cap (FIG. 6; 601, FIG. 7; 702) in place; a fourth element of an upper lid (FIG. 6; 601, FIG. 7; 703); a fifth element of an one inlet tubing for inflow (FIG. 7; 704); a sixth element of about two outlet tubings (FIG. 7; 705); in a housing with a thickness; and with utility in therapy of HTM disease.

Another aspect of the present invention is a method for inserting and using an artificial TM clinical device comprising the steps of: inserting said device using one of a first maneuver including a steps of removing the TM using methods known to those of skill in the art; and of replacing the TM with said artificial TM clinical device; and a second maneuver of inserting the device outside the eye; and treating said HTM disease.

DESCRIPTION OF FIGURES

These and other features of this invention will be more readily understood from the following detailed description of the various aspects of the invention taken in conjunction with the accompanying drawings in which:

FIG. 3A is a top view schematic illustration of the 3-D micro- and nanostructured scaffold. Pore 301.

FIG. 3B is a side view schematic illustration of the 3-D micro- and nanostructured scaffold.

FIG. 3C is a 3-D schematic illustration of the 3-D micro- and nanostructured scaffold. (L1) The length of the square pore (L2) The width of the square pore (W) The beam size (H) The thickness of the scaffold.

FIG. 4 is a schematic diagram of the fabrication of 3-D micro- and nanostructured scaffold array of the present invention using photolithography: (a) Release Layer 401 treatment on previously cleaned silica wafer 402; (b) Coating of substrate 403; (c) Exposure through a mask 404 and post-exposure bake; (d) Develop; and (e) Create 3-D micro- and nanostructured scaffold that fit in a microtiter plate for HTM cell growth; where (1) Release Layer (2) 401, Wafer 402, (3) Substrate subject to micro- and nanofabrication 403, (4) Mask 404.

FIG. 6A is an exploded is a cross-sectional view of a human trabecular meshwork device for clinical use, where 601 are the device covers (bottom cap and upper lid), 602 is the scaffold holder.

FIG. 6B is a cross-sectional view of the human trabecular meshwork device for clinical use, each in accordance with the present invention, where 601 are the device covers (bottom cap and upper lid), 602 is the scaffold holder; 604 is a first filter, 107 is the HTM cells, 108 is the SC cells, 607 is a second filter, 608 is an inflow channel, 609 is an outflow channel.

DETAILED DESCRIPTION OF THE PREFERRED EMBODIMENT

Overview

Definitions

Figure 1:
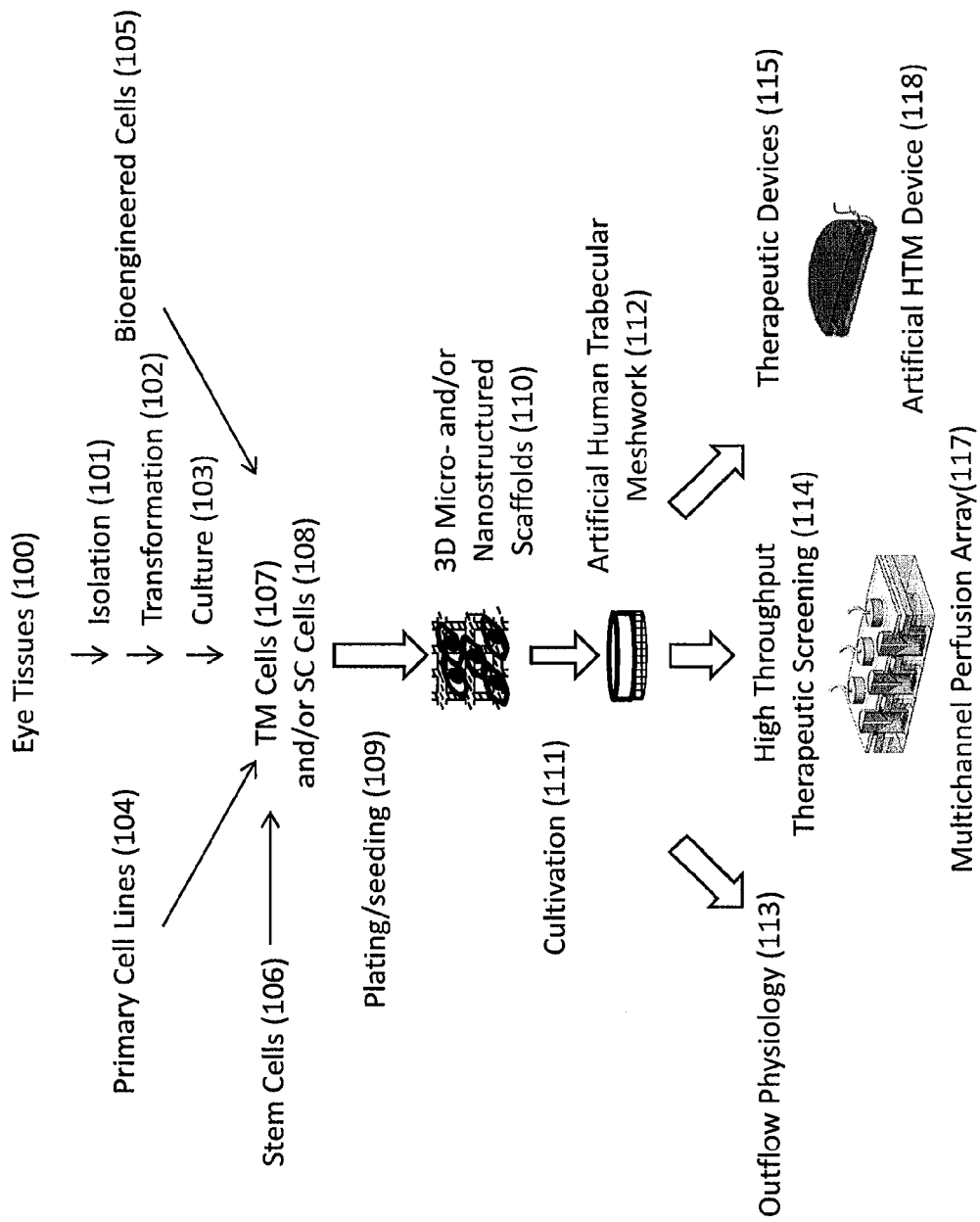
FIG. 1 is a process flow diagram that shows the work flow to generate artificial trabecular meshwork [TM], and some exemplary potential end uses. Cell lines 104; primary cells isolated from eye tissues 100 through isolation 101; transformation 102; culture 103; cells derived from stem cells 106; bioengineered or genetically engineered cells 105; TM cells 107; SC cells 108; plating or seeding 109; 3-D micro- and nanostructured scaffolds 110; culturing 111; artificial human trabecular meshwork system 112 into a single channel perfusion chamber or an assembled multi-channel perfusion array 117; an artificial HTM device 118; outflow physiology 113; high throughput therapeutics screening 114; therapeutic devices 115.

In order to provide a clear and consistent understanding of the specification and claims, including the scope to be given such terms, the following definitions are provided. Any terms that are not specifically defined in this or other sections of this patent application have the ordinary meaning they would have when used by one of skill in the art to which this invention applies at the time of the invention.

As used herein, all temperatures are in degrees Celsius (° C.), unless otherwise specified.

As used herein, human trabecular meshwork or HTM cells include all cells of the Trabecular Meshwork [TM]. It may include all cells that play an active role in the intraocular fluid outflow or exit pathway, including but not limited to those from the juxtacanalicular and corneoscleral region of the trabecular meshwork of the eye as well as Schlemm's canal cells.

As used herein, the choices of cell sources of HTM cells can be various including but not limited to HTM cells from cell lines, primary HTM cells isolated from tissues, HTM cells derived from stem cells (e.g., embryonic stem cells, adult stem cells, induced pluripotent stem cells), and genetically engineered cells. Choices of HTM cells may include epithelial cells, epidermal cells, endothelial cells, smooth muscle cells, stromal cells, neural cells, stem cells, but are not necessarily limited to the HTM cell types listed herein.

As used herein, primary HTM cells are cells derived from living tissue.

As used herein transformed HTM cells are cells immortalized in culture.

As used herein, intraocular fluid, may also mean aqueous humor; and intraocular fluid pathway or intraocular outflow pathway or intraocular exit pathway may also mean aqueous humor pathway or aqueous outflow pathway or aqueous humor outflow. These terms will be used interchangeably herein.

As used herein, human means any mammal including but not limited to humans, and animals, e.g., rhesus monkeys, other monkeys, sheep, pigs, rabbits, rats, and mice.

As used herein, substrate means a material subjected to micro- and/or nanofabrication for example SU-8 or any material including but not limited to polymeric, ceramic, metallic, semiconductor, composite material.

As used herein, scaffold, 3-dimensional (3-D) micro- and nanostructured scaffold, or SU-8 scaffold may mean a micro- or nanopatterned material, micro- or nanofabricated material, micro- or nanoporous materials, or their hybrid for example a porous SU-8 scaffold or any material which responds to appropriate fabrication and HTM biocompatible coating techniques known to those skilled in the art by achieving desired properties of supporting desired 3-D HTM cell and Schlemm's canal [SC] cell growth and attachment, which may include macroporous, flexible, free-standing, synthetic or natural biomaterial scaffolds and their hybrids. The scaffold may include a biocompatible, epoxy-based, negative tone photoresist that can be micro- or nanopatterned into custom designed micro- and/or nanostructures using photolithography, for example SU-8. It may include a material that has previously been used as a cell culture substrate, but not necessarily for 3-D HTM cell culture, including but not limited to polystyrene, polyester, polypropylene, polycarbonate, polyamide, polyethers, polyimide, polymethylmethacrylate (PMMA), polydimethylsiloxane (PDMS), hydrogels, inorganic materials. It may include any scaffold material that may be reproducibly fabricated into micro- or nano structures with over a wide range of thicknesses, produce high aspect-ratio structures without collapsing, and can be transparent, allowing for easy monitoring of HTM and SC cell growth and behavior, for example SU-8. The scaffolds may be formed by manipulation with predetermined pore and beam width and sizes. The pore sizes and beam widths may be uniform. The scaffolds may include a micro- or nanofibrous material that is fabricated or synthesized using electrospinning, self-assembly or phase separation. The 3-D micro- and nanostructured scaffolds may be used alone or combined with HTM biocompatible coating for a choice of 3-D HTM cell proliferation, including but not limited to those used herein for example epithelial cells, endothelial cells, smooth muscle cells, stromal cells, neural cells, and stem cells.

As used herein, micro- or nanoporous materials used alone or in hybrid combinations may mean microfabricated membranes, filters, permeable films, micro- or nanofluidic devices including but not limited to SU-8, track-etched membranes, mixed cellulose membranes, polystyrene membranes, poly(L-lactic acid) membranes, poly(lactic-co-glycolic acid) membranes, polycaprolactone membranes, polyimide membranes, polyamide membranes, polyethersulfone membranes, polyethersulfone membranes, poly(vinylidene fluoride) membranes, silk fibroin membranes, hydrogel membranes (e.g., alginate, chitosan, gelatin, collagen, hyaluronic acid, or composite), nanocrystalline silicon membranes, alumina membranes, nanofibrous membranes, and composite membranes.

As used herein, photolithography may include the process used to design and pattern a biocompatible 3-D micro- or nanostructured scaffolds on a photoresist (for example SU 8) and a variety of microfabrication processes including but not limited to microembossing processes, dip-pen nanolithography, colloidal lithography, electron beam lithography, nanoimprint lithography to achieve an optimal 3-D HTM in vitro cellular structure. It means any controllable method to fabricate tissue scaffolds with a well-defined 3-D architecture that can be used to better elucidate the effect of structure parameters such as pore geometry and pore size on HTM cell and SC cell growth in 3-D scaffolds.

As used herein, coating on a 3-D micro- or nanostructured scaffold means any biomacromolecule or synthetic coating on a 3-D micro- or nanostructured scaffold that may support any HTM or SC cell growth and proliferation for several hours, days, months or years into a functional trabecular meshwork [TM], for example, a confluent HTM/SC cell meshwork-like construct. It may include, but is not limited to gelatin, poly-L-lysine, laminin, collagen or other molecules known to those skilled in the art.

As used herein, beam width means the grid spacing between two adjacent pores.

As used herein, beam height means the thickness of the 3-D micro- and nanostructured scaffold.

As used herein, an artificial trabecular meshwork (artificial TM) is an in vitro 3-D HTM cell system model in which HTM and/or SC cells grow on a 3-D micro- or nanostructured scaffold to recreate a functional trabecular meshwork [TM], for example, a confluent HTM/SC cell meshwork-like construct.

Figure 2:
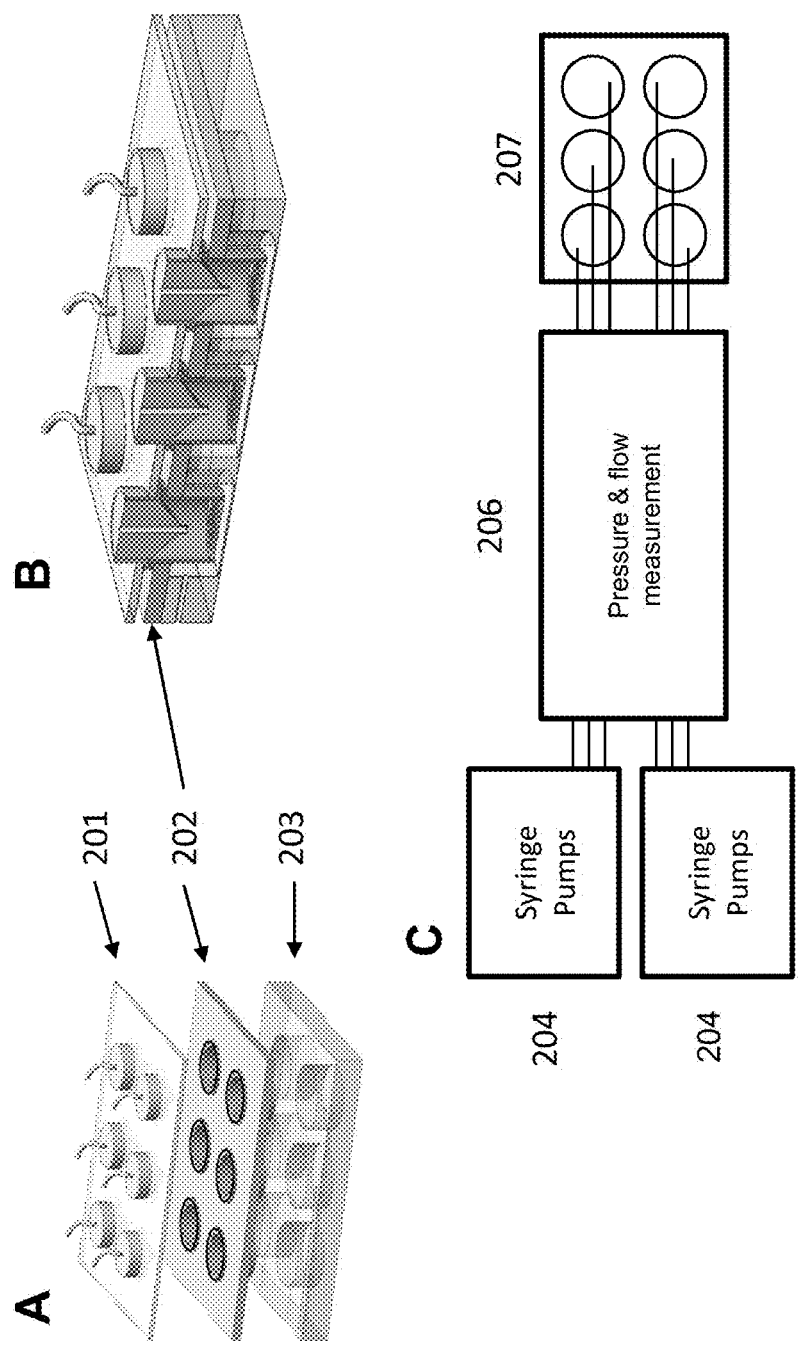
FIG. 2 is a rendering of components needed for a functional high-throughput screening artificial TM: (a) Exploded view; (b) Cross-sectional view of multi-channel perfusion array; (c) The artificial TM-based high throughput screening system. Re-usable lid structure with fluidic inlets 201; disposable cell-culture insert with a porous substrate 202 supporting an artificial HTM; re-usable effluent wells 203; fluid delivery devices 204; pressure transducer and flow monitors 206; perfusion chamber 207 incorporating a multi-channel perfusion array.

As used herein, a perfusion chamber is any construction housing that provides a feasible way to combine the elements in this invention in a controlled environment in perfusion experiments as shown in FIG. 2. It may include but is not limited to a scaffold holder construct (FIG. 2A-B; 202) supporting an in vitro 3-D HTM cell system model with pre-defined, well-controlled, uniform pore size, shape and beam width; an integrated pressure transducer and/or flow sensor (FIG. 2C; 206) for sensing the transmembrane pressure (and/or flow) under constant flow (or pressure) conditions at a predetermined flow (or pressure) rate, for a predetermined time period, at a constant temperature; a construction for investigation and recording of outflow physiology.

As used herein, a scaffold holder is a filter holder, array of filter holders, or a microtiter plate that secures the artificial trabecular meshwork in the perfusion chamber and allows performing the perfusion experiments in a high throughput fashion (FIG. 2).

As used herein, SEM is scanning electron microscopy.

As used herein, DAPI is 4',6-diamidino-2-phenylindole.

As used herein MEM is minimal essential medium.

As used herein, cytoskeleton includes but is not limited to F-actin, and other cytoskeletal proteins.

As used herein, a 3-D HTM structure may include but is not limited to HTM cell interaction, enhanced HTM cellular interactions, HTM cell-cell and cell-ECM, cell secreted extracellular material, and HTM cell processes.

As used herein, transmembrane may include a 3-D micro and nanostructured scaffold structure as constructed in this invention with or without a seeded cell culture, which may have been cultured over several hours or days and cells may have proliferated on a 3-D micro and nanostructured scaffold with several layers of TM/SC cells. Cell adhesions between HTM cells provide dynamic, bidirectional links between the extracellular matrix and the cytoskeleton.

As used herein, Lat-B, unless otherwise specified, includes but is not limited to Lat-B and other well-documented or novel, innovative HTM therapeutic agent, which may prevent, cure, or ameliorate an outflow system-related disease. It may include but is not limited to drugs, for example, Lat-B or a novel agent that may cause a minor or marked drop in perfusion pressure or intraocular pressure or improve aqueous flow or improve intraocular exit pathway channels and lower intraocular pressure therein.

As used herein, intraocular pressure (IOP) means the pressure caused by the fluid inside the eye that helps maintain an eye. There is some diurnal and seasonal variation to control the IOP within the correct physiological range necessary to maintain the anatomical conditions suitable for optimal refraction and thus vision.

DESCRIPTION OF THE EMBODIMENTS

The present invention overcomes the drawbacks in the prior art that make current human trabecular meshwork (HTM) outflow facility studies unsuitable for a uniform, well-defined, controllable, low cost, high throughput 3-D HTM screening and to provide a novel therapeutic device that can regulate IOP. The following features serve the great need for a bioengineered, functional, in vitro 3-D HTM model for a screening procedure, for example, glaucoma drug screening. A model according to the present invention would advance the understanding of the HTM and provide a platform for future low-cost, less invasive, novel studies related to the eye, leading to drug discovery and effective treatment of diseases of eye, for example, glaucoma.

This invention overcomes a screening drawback which is over a century old: In conventional in-vitro systems, cells are grown on flat glass, tissue culture plastics, or commercially-available filters, only allowing monolayer or single cell layer growth of HTM cells. In this invention, the construction of a micro- and/or nanopatterned 3-D micro- and nanostructured scaffold allows for multiple HTM cell layers to form (FIG. 5C), much like those observed in the in-vivo environment. The present invention, therefore, serves a valuable, century old need for a multicellular transmembrane screening option. In addition, it allows development of 3-D co-culture system that will further simulate the human outflow pathways.

Interestingly, the diameter of the beams revealed in previous SEM work (Polansky et al., Ophthalmology. 1984 June; 91(6):580-95) of the intricate in vivo microenvironment of the HTM complex meshwork match the micropatterned width of beams (FIG. 3B; W) that make up the 8-15 μm and in a preferred embodiment 10-12 μm pores (FIG. 3A; 301) used in this in vitro work in this invention, which might explain why this 3-D micro- and nanostructured scaffold structure shows good HTM cell adhesion and proliferation. The pore size range with corresponding width of beams of the present invention are features for an optimal artificial TM. This invention recreates an in vitro structure (FIGS. 3A, 3B, 3C, 9), for the seeded cells to use as a "guide" (FIG. 11) while mimicking the in vivo HTM morphology, in which the pore sizes and width of beams are created via the intricate adhesions of various types of interacting cells of the HTM and their secreted extracellular matrix.

Figure 13:
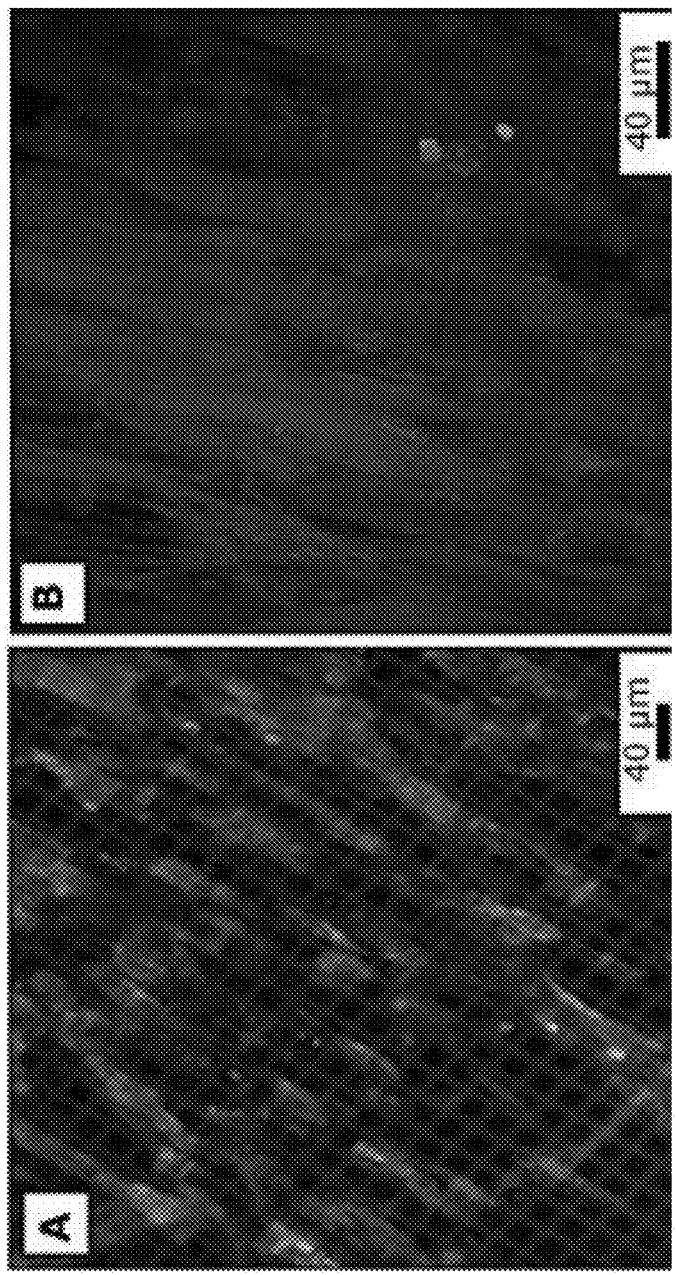
FIG. 13 is confocal micrographs of HTM cells grown on gelatin-coated SU 8 3-D micro- and nanostructured scaffolds showing HTM markers: (A) α-smooth muscle actin (α-SMA), and (B) αB-crystallin.
Figure 14:
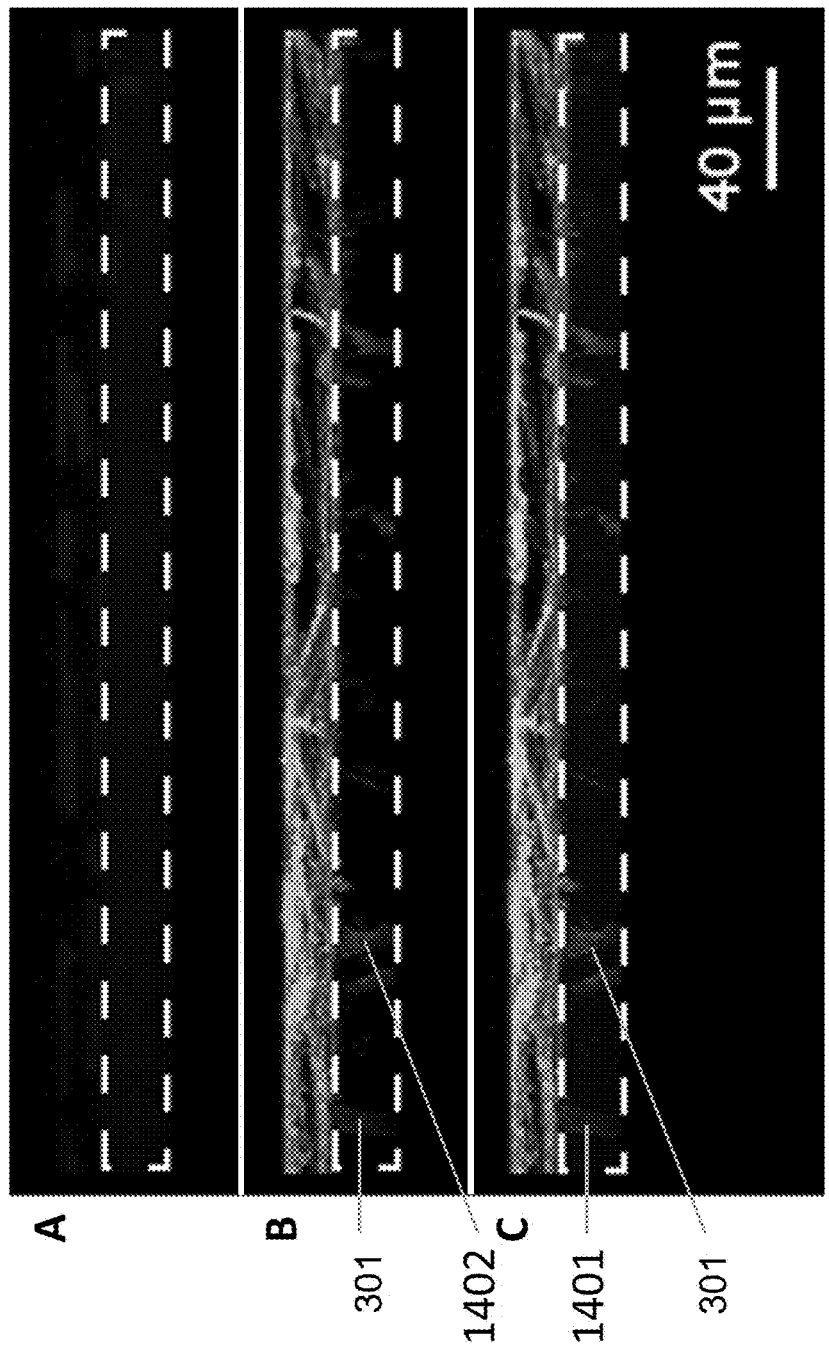
FIG. 14 is a 3-D confocal reconstruction of HTM cells grown on a gelatin-coated SU-8 3-D micro and nanostructured scaffold with 12 μm pores. 4',6-diamidino-2-phenylindole (DAPI) stained nuclei (A). F-actin expression (B). Merged images (C). The SU-8 3-D micro- and nanostructured scaffold exhibits autofluorescence and is indicated by the dashed-line rectangles. Cellular processes extending vertically into scaffold pores 301. Scale bar=40 μm.
Figure 15:
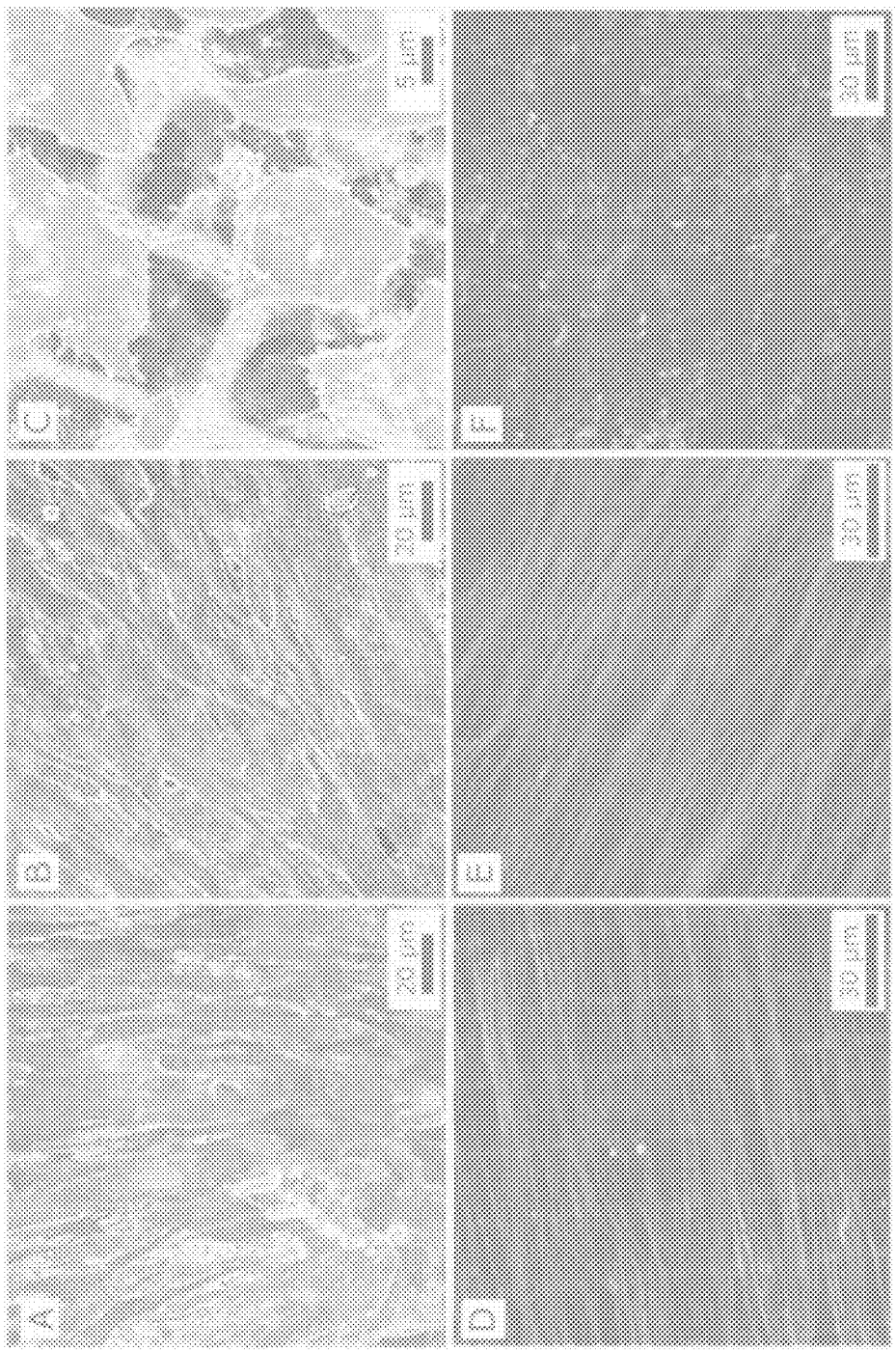
FIG. 15 is HTM cells grown on SU-8 3-D micro- and nanostructured scaffolds (A and D), after perfusion with medium (B and E), and after perfusion with medium and Lat-B (C and F). SEM micrographs (A-C). Confocal micrographs showing F-actin cytoskeleton (D-F).
Figure 16:
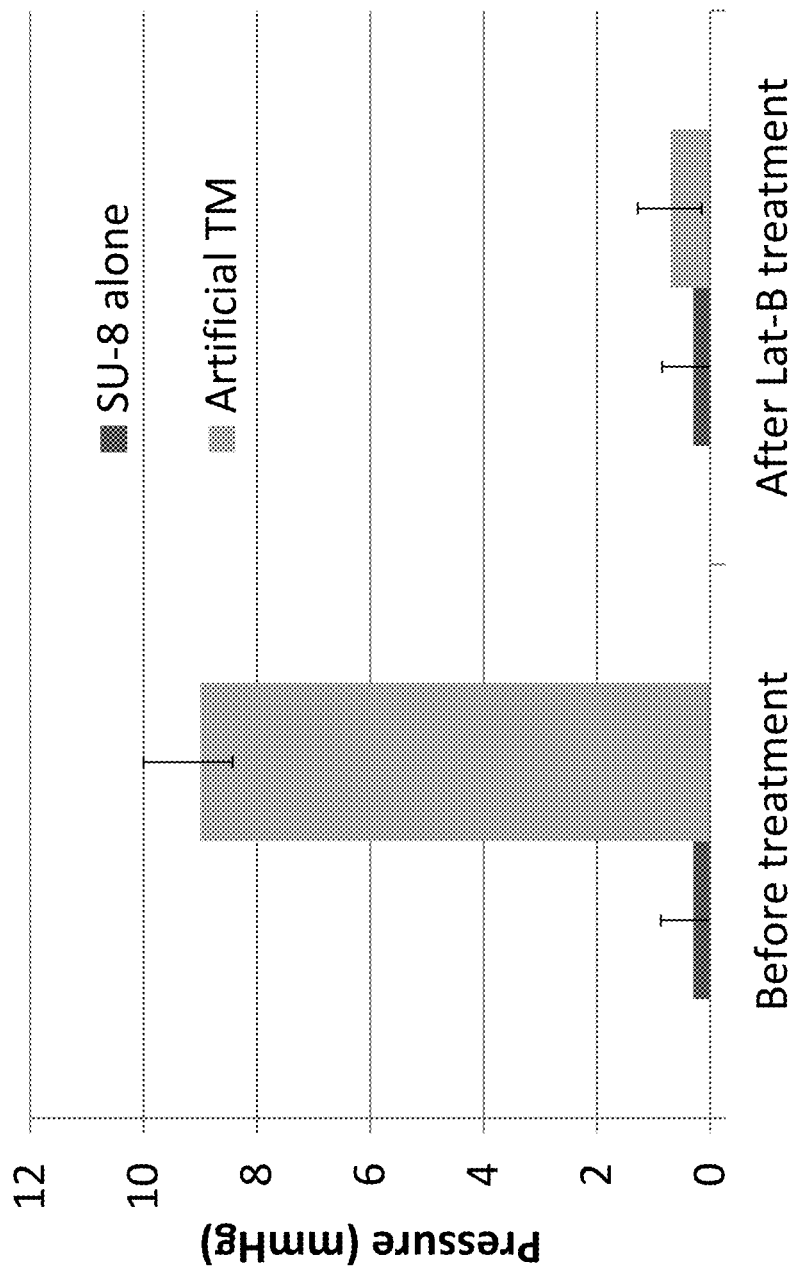
FIG. 16 is the effect of Lat-B on flow resistance. The fact that perfusion pressure of the artificial trabecular meshwork [TM] decreased dramatically after Lat-B treatment indicates decreased flow resistance in the artificial TM in response to Lat-B treatment.

Such a model as in this present invention would advance the understanding of the HTM and provide a platform for future low-cost, less invasive, novel studies related to the eye, for example leading to innovative drug research and discovery (FIGS. 15, 16). Scaffolds with a well-defined 3-D architecture can be used to screen the effect of structure parameters such as pore geometry and pore size on HTM cell growth in 3-D micro- and nanostructured scaffolds, under controlled conditions (FIG. 8-16). A perfusion chamber to provide controlled conditions was created in the present invention as shown in FIG. 2. Also, models based on the current invention may be adapted to provide an artificial trabecular meshwork (FIGS. 6 and 7) that a physician might use to insert to replace the defective trabecular meshwork of a patient, inside or outside the eye of a patient in addition to prescribing eye drops for eye diseases such as glaucoma.

A perfusion chamber to provide controlled conditions was created in the present invention as shown in FIG. 2 to provide such controlled conditions as temperature and flow rate, while allowing for variables in pore size and width of beam of scaffold along with other micro- or nanopatterning to be compared. The concept in this invention is incorporated into a high-throughput system set up, allowing for arrays of artificial HTM in experimental screening efforts (FIG. 2). The artificial HTM of the present invention allows for high throughput screening, which in turn, enables restriction of the use of live animal eye research and decreases the need for live or deceased natural eye donors.

A major point of novelty of the present invention is in the micro- and nanostructure of the 3-D micro- and nanostructured scaffold. A micropatterned 3-D micro- and nanostructured scaffold scaffold having a well-defined 3-D architecture (FIGS. 3, 4, 5 & 9) (that can be used to better elucidate the effect of structure parameters on HTM cell growth and proliferation) was constructed using photolithography for uniform pore geometry and optimized pore and beam size, as illustrated in FIG. 4. The material used to create the scaffold may be variable, although SU-8 was chosen as an ideal substrate to fabricate porous 3-D micro- and nanostructured scaffold. A hybrid material may also provide a scaffold, as long as it results in a suitable, functional artificial HTM, as per the concept of this invention.

The novel microstructure of the scaffold in this invention could vary the range of the pore size. The range of pore size found to be ideal herein was 10-12 μm, while 1-7 μm resulted in inferior results and above 14 μm exhibited suboptimal results. For this invention, a microstructure pore size range of 10-12 μm is optimal to create a functional artificial HTM.

The resulting micropatterned 3-D micro- and nanostructured scaffold (FIGS. 9, 10) constructed via the process discussed herein (FIG. 4) resulted in a 3-D square pore of uniform size, as illustrated in FIG. 3. A nanopatterned 3-D micro- and nanostructured scaffold may be constructed using the same concept (FIG. 3A, 3B, 3C).

Figure 5A:
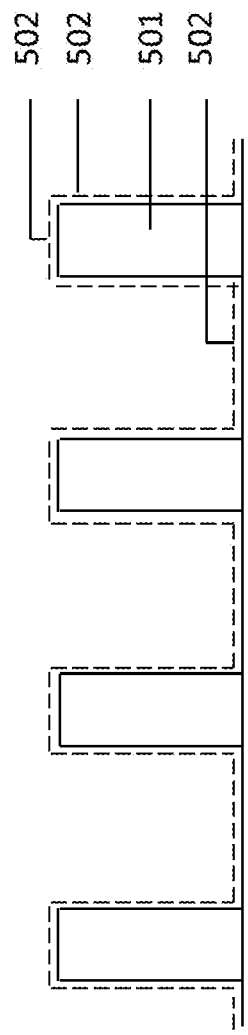
FIG. 5A is a schematic illustration of the development of a bioengineered human trabecular meshwork (HTM) in a sectional view of the HTM cells growing on a HTM biocompatible coated scaffold: Day 0, HTM cell seeding; where 3-D micro and nanostructured scaffold 501; HTM biocompatible coating 502.

Conditions for optimal HTM cell growth on the micropatterned 3-D micro- and nanostructured scaffold were enhanced by coating the scaffold with a HTM biocompatible coating optimal for HTM cells as shown in FIG. 5A.

Conditions for optimal HTM cell growth were experimented with and the best conditions selected herein were those suitable for the specifications listed herein. These are only examples of optimal conditions, and the invention is not limited by these, but instead, incorporates all feasible conditions.

Utility in Perfusion Studies

In a preferred embodiment, incorporating the primary features of the present invention, a flow system apparatus for the controlled flow pressure measurement was constructed as shown in FIG. 2. It can be integrated easily to enable low-cost high throughput assays within an addressable 3-D environment (FIGS. 1 & 2), which is attractive for use in understanding of outflow physiology, drug screening and other therapeutic screenings.

1. The flow system apparatus (FIG. 2) incorporating the principles and features of this invention is contained within a controlled environment, which herein comprises of a stand-alone perfusion chamber, with a cell growth medium entry system (FIG. 2c; 204) and a screening agent (for example a glaucoma drug) entry system (FIG. 2c; 204) as shown in FIG. 2c. The system allows for the screening agent to be added to the perfusate at a pre-determined concentration for a pre-determined number of hours. This 3-D structure of the bioengineered in vitro HTM cell system in the present invention allows for the HTM cells to behave in a "physiological manner" mimicking preferred in vivo conditions in a controlled environment.

2. Includes an integrated pressure transducer (FIG. 2c; 206), an integrated pressure sensing system while maintaining a constant flow rate and a pressure measurement system at different flow rates for calculation of the outflow facility of the bioengineered HTM.

3. Includes the bioengineered HTM, a micropatterned, HTM biocompatible coated 3-D micro- and nanostructured scaffold with HTM cells providing flow resistance (FIG. 5C) or without HTM cells (FIG. 5A) providing no significant resistance to flow. The construction of a scaffold holder is shown in FIGS. 2a and 2b. This artificial HTM is set up in the scaffold insert (FIG. 2a; 202).

4. Includes the bio-compatible scaffold holder array construction (FIGS. 2a, 2b, 2c) as shown in FIG. 2. The 3-D micro- and nanostructured scaffold with or without HTM cells were secured in the scaffold holder inside the perfusion chamber. Lid 201, scaffold insert 202, effluent well 203.

Figure 8:
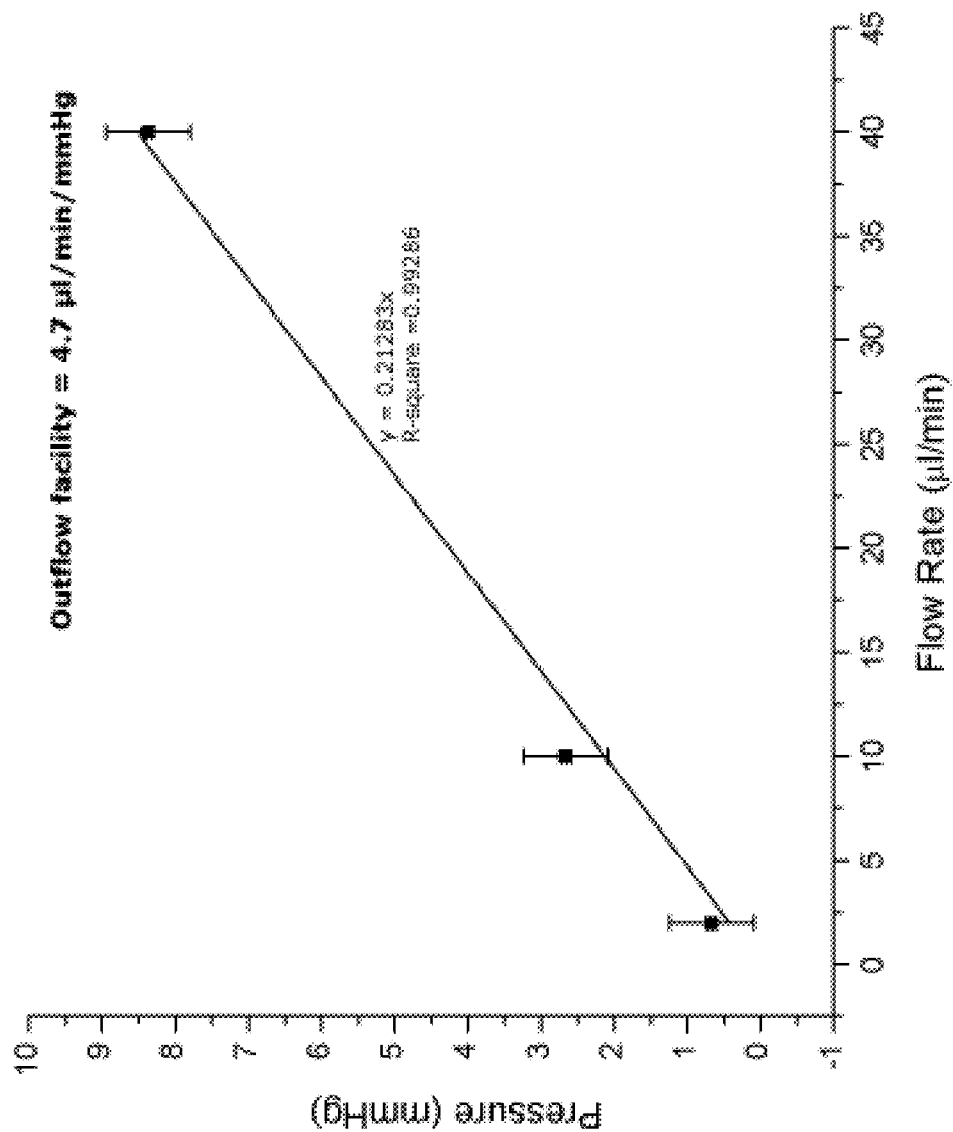
FIG. 8 is a determination of outflow facility of bioengineered HTM on 3-D micro- and nanostructured scaffolds.
Figure 9:
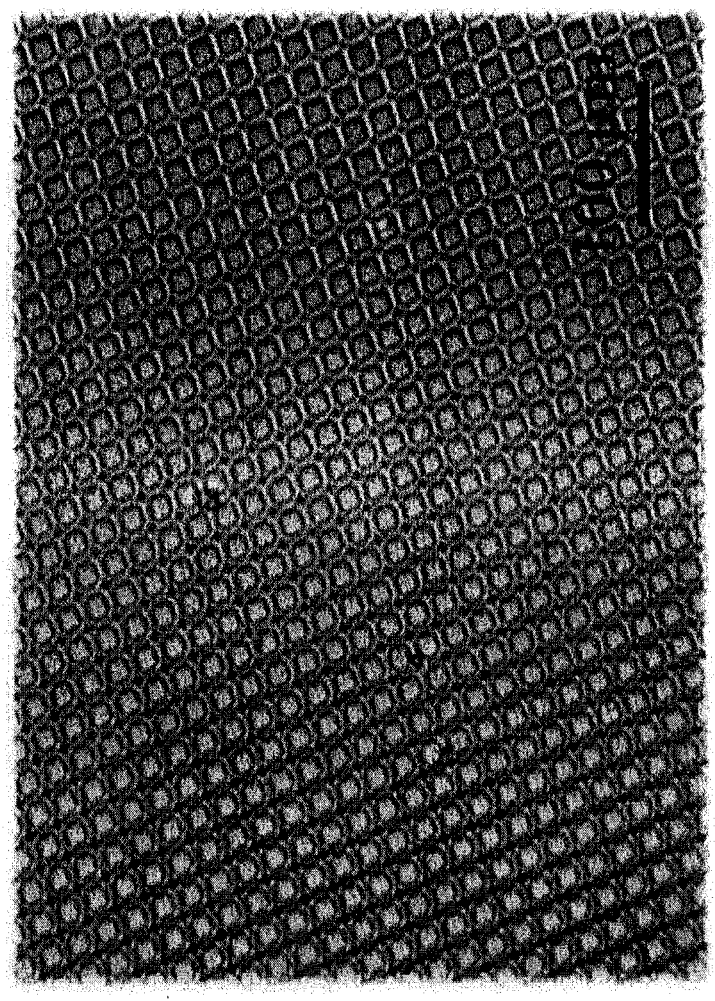
FIG. 9 is a Scanning Electron Micrograph (SEM) image (top view) of a freestanding 3-D micro- and nanostructured scaffold.
Figure 10:
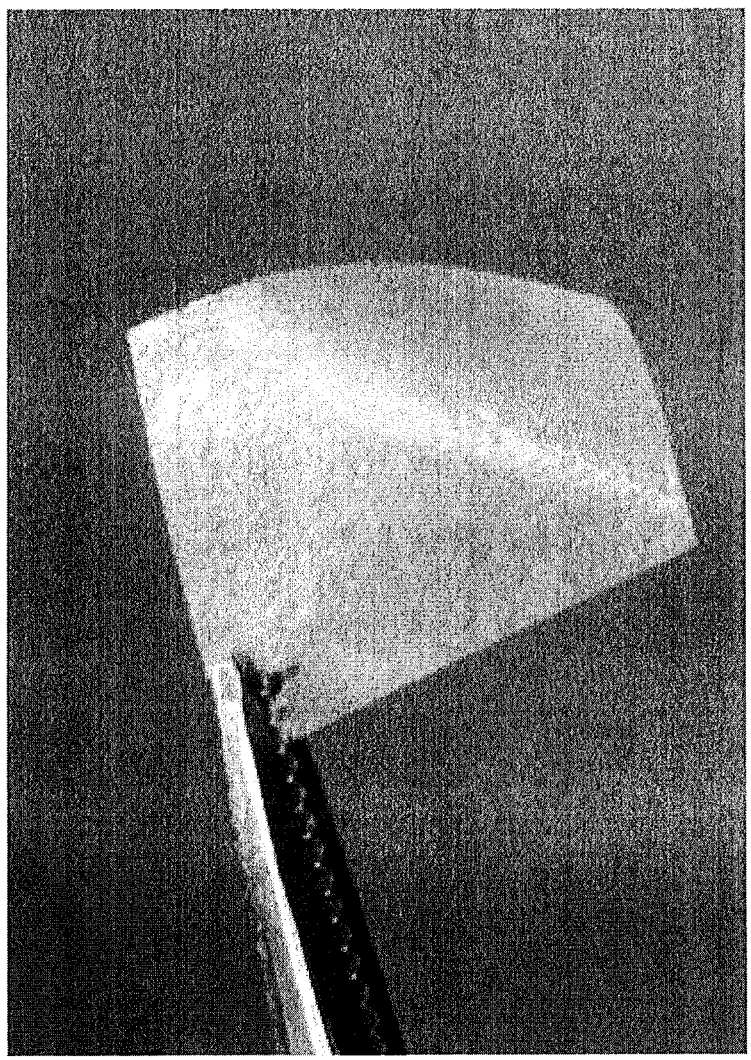
FIG. 10 is an optical image of a freestanding 3-D micro- and nanostructured scaffold.

5. This flow system allowed for simultaneous control of the flow and measurement of the transmembrane pressure, permitting the exploration of the outflow characteristics of the in vitro HTM model. Pressure measurements at different flow rates allowed for calculation of the outflow facility of the bioengineered HTM. Transmembrane pressure (P) was plotted as a function of flow rate (F) and the linear regression gave rise to the slope which was the value of change of transmembrane pressure ($\Delta P$)/the change of flow rate ($\Delta F$) (FIG. 8).

6. Since the outflow facility could be determined by $\Delta F/\Delta P$, the outflow facility was given by the inverse of the slope.

Figure 11:
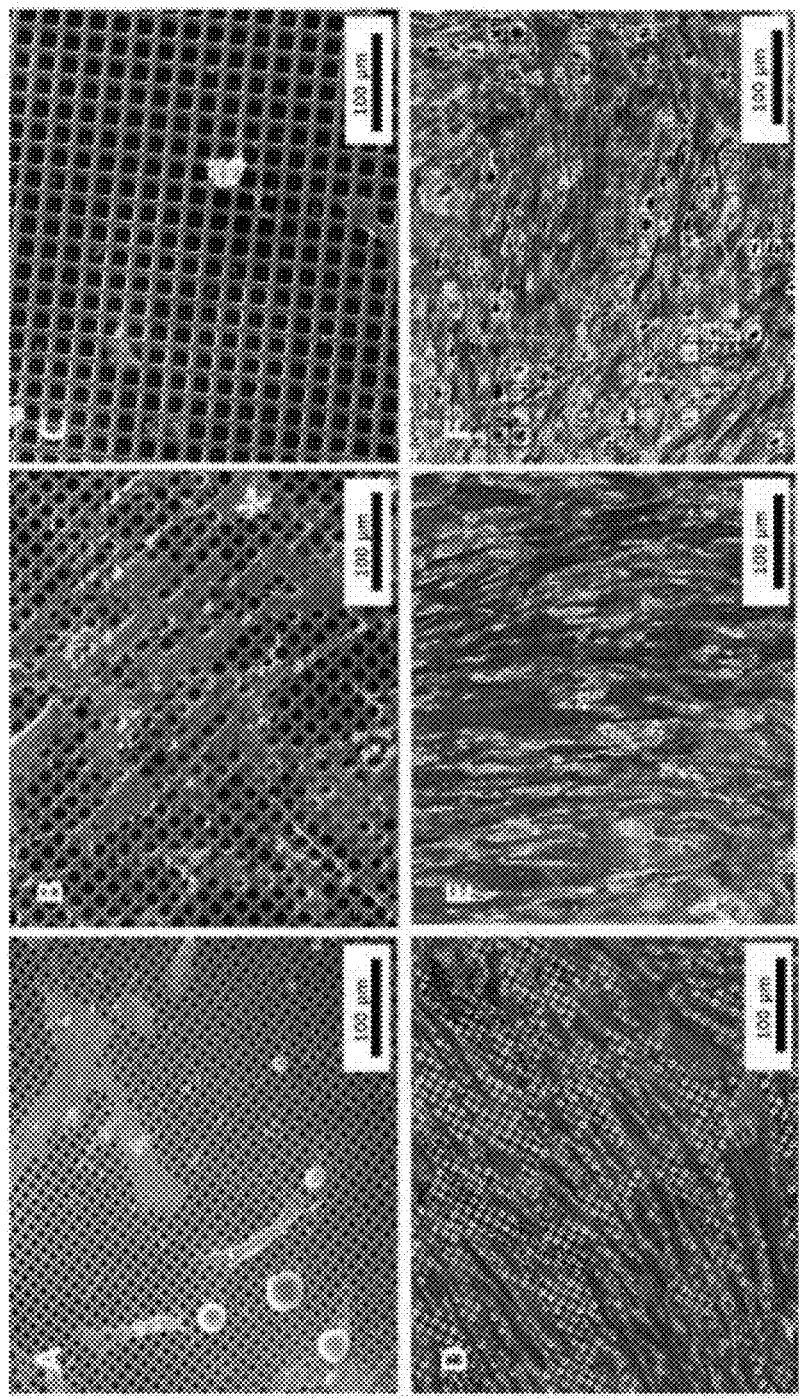
FIG. 11 is SEM images of HTM cells grown on gelatin-coated SU-8 3-D micro- and nanostructured scaffolds of different pore sizes for 7 days: (A-C) Seeding density of $1\times10^4$ cell/cm$^2$; (D-F) Seeding density of $4\times10^4$ cell/cm$^2$. (A and D) pore size=7 μm. (B and E) pore size=12 μm. (C and F) pore size=15 μm.

7. Fourteen days prior to perfusion measurements, HTM cells (for example $4 \times 10^5$ cell/scaffold) were seeded on HTM biocompatible coated scaffolds (for example SU-8) having a pre-determined pore size range. The seeding density and cell source may vary (FIG. 11).

8. At day 14, samples were placed in the perfusion chamber and were perfused in the apical-to-basal direction (for example at 2, 10 and 40 μm/min) for several hours (for example, 24 hrs), respectively, with perfusion media (for example, comprising Dulbecco's modified Eagle's medium (DMEM) containing 0.1% gentamicin). The temperature was kept constant (for example, at 34° C.). Back pressures were continuously monitored with a pressure transducer and recorded.

9. For the treatment with a screening agent (for example, Lat-B), once a stable baseline pressure was reached through perfusion of media and Hank's balance salt solution (HBSS) as described above, samples were then perfused with the screening agent (for example 20 1-1 M Lat-B in HBSS at the same constant flow and temperature (for example for 4 hrs) FIG. 16).

10. After detecting the effect of the screening agent the cells can be perfused again with media to ensure that outflow facility reverts to prior values.

11. Follow up cell characterization studies may be conducted as desired with standard techniques well known to those of skill in the art. For this invention, samples were fixed and stained for SEM and confocal image analysis as described herein (FIGS. 11-15).

All chemicals were purchased from Sigma-Aldrich unless otherwise specified. Primary HTM cells, isolated from the juxtacanalicular and corneoscleral region of the human eye, were either purchased from ScienCell Research Laboratories (Carlsbad, Calif.) or cultured from donor tissue from corneal transplant rims. HTM cells were cultured in Improved MEM (Cellgro, Manassas, Va.) with 10% fetal bovine serum (ScienCell Research Laboratories, Carlsbad, Calif.).

A Medical Device Utility for the Artificial TM

A "physiologic" bypass of the outflow pathways would be expected to reduce IOP while maintaining the functionality of the TM and not relying on the control of the fibrotic response induced by current glaucoma surgery. For practical reasons, this bypass of the outflow pathways can be moved outside of the eye, making implantation of the device easy for eye surgeons who are trained to insert seton devices. However, implantation will require additional training as the aqueous humor will need to be directed into the SC to re-establish the physiologic flow of aqueous humor.

A device suitable for implantation in humans (FIG. 7) or other mammals can be constructed of, for example, either polypropylene (inflexible) or medical grade silicone (flexible). The device can be roughly circular or ovoid (similar to a glaucoma seton device) and can have fixation holes anteriorly for suturing to the sclera and at the sides for growth of fibrous tissue over time (and thus additional fixation). The total height will be between 0.5 and 2 mm while the area will be 150-300 mm$^2$ (this is an area calculation assuming that filtration area occupies ~50% of the total device area. This would provide ~115 mm$^2$ for filtration which is roughly similar to the area of the human TM facing the anterior chamber). Although backflow will not be prevented, filters below and above the cell bi-layers will prevent HTM cells from potentially moving back into the eye and SC cells flowing out (FIG. 6, 604, 607). Devices will be tested ex-vivo for determination of resistance to flow without and with cells loaded.

Thin polyimide (100-300 μm diameter) perforated (outflow) and silastic (inflow) tubes will direct fluid in and out of the central portion of the device. The inflow tube will be placed in the anterior chamber as for a regular glaucoma seton tube. The outflow tubes will be inserted in the SC after 360 degree cannulation using an iScience or other similar catheter. The device will remain in place for the duration of the patient's life or can be easily replaced if it malfunctions or for other reasons.

In one aspect of the current invention, the bioengineering of the substrate comprises optimizing the property of the substrate to yield a trabecular meshwork (TM) that mimics the physiological function of TM found in vivo.

In one aspect, this substrate property comprises at least one of composition and geometry of scaffolds. In another embodiment, the 3-D scaffolds are porous. In yet further embodiments the substrate comprises of a material including but not limited to a porous membrane or filter, a photodefinable material, a track-etched membrane or filter, a nano fibrous material or SU 8.

In another aspect, the geometry of 3-D micro- and nanostructured scaffolds of the invention exhibit a grid spacing of approximately between 0.1 and 20 microns. In another aspect, the pore size of the 3-D micro- and nanostructured scaffolds is approximately between 0.1 and 20 microns.

An embodiment of the invention provides for the method of bioengineering a trabecular meshwork [TM] that are derived from the 3-D micro- and nanostructured scaffolds of the current invention. Given their interesting similarity to the beam width and height structure observed in SEM of in vivo trabecular meshwork, the 3-D micro- and nanostructured scaffolds of the current invention can be modified for both high-throughput screening and therapy. In one embodiment, the optimizing a property that mimics the physiological function of the TM found in vivo is by favoring the culturing of HTM cells on the 3-D micro- and nanostructured scaffolds. In further modifications of the invention, the culturing step comprises optimizing a cell seeding density, wherein the cell seeding density is at least 1×10$^4$ cells/cm$^2$. The technology of cell seeding is well known to those of skill in the art. Various types of HTM cells may be suitable for the purposes of this invention, appreciated by those of skill in the art. In a further embodiment, the culturing step comprises at least 7 days of culturing of seeded cells yielding at least one sheet of cultured cells, whereby forming a human trabecular meshwork system [TM]. In a yet further embodiment, the cultured cells are characterized to assess their similarity to in vivo HTM cells by standard assessing cell morphology techniques known to those of skill in the art. The cultured cells in this invention exhibit a spindle shape and express at least one of alpha-smooth muscle actin, myocilin and alpha B-crystalline.

One aspect of the present invention comprises further treating the bioengineered TM with at least one anti-glaucoma agent; and investigating an outflow facility of the cultured cells.

Another aspect comprises an investigating step comprising using a pressure sensing system, wherein the pressure sensing system is integrated with a perfusion chamber or the pressure sensing system is a stand-alone perfusion chamber.

In one aspect of the invention the pore size ranges from 0.1 microns to 8 microns, 8 microns to 14 microns and 14 microns to 30 microns, and more preferably approximately 7, 12 and 15 μm and most preferably for HTM cell size of current invention approximately 10 microns to 12 microns.

An HTM with a pore size range of 5-over 15 μm

An HTM with an optimum pore size range of 10-12 μm

An HTM with a pore size of 12 μm

In one aspect of the invention the three dimensional porous trabecular meshwork that mimics the in vivo TM having beam widths approximately ranging from 0.1 microns to 20 microns and more preferably approximately 3.4±0.1 μm, 7.3±0.1 μm and 5.2±0.1 μm.

An HTM with a seeding density of 4×10$^4$ cells/cm$^2$

An HTM with a seeding density of at least 2×10$^4$ cells/cm$^2$ and preferably 4×10$^4$ cells/cm$^2$ In another aspect of the present invention, an HTM is constructed with a 14 day HTM cell culture.

The HTM cell culture in this invention is facilitated by pore size, beam width and beam height. In a preferred embodiment the beam width and height is about 0.1 μm to about 20 μm. In a further embodiment the beam width and height is about 3.4±0.1 μm, 7.3±0.1 μm and 5.2±0.1 μm ($p<0.05$).

In one embodiment method for a high-throughput screening artificial HTM screening comprises achieving the optimal 3-D thickness of the artificial HTM of at least around 20 microns to mimic the structure and function of an in vivo TM.

In another aspect of the present invention a method for a high-throughput artificial HTM screening system comprising maintaining said constant flow rate through a said pressure transducer from about 0.1 μl/min to about 15 μl/min to study the effect of experimental agents on the HTM aqueous flow facility. In a further embodiment, comprising maintaining said constant flow rate through a said pressure transducer at about 15 μl/min to about 30 μl/min; and in a yet further embodiment maintaining said constant flow rate through a said pressure transducer at about 30 μl/min to about 60 μl/min to study the effect of experimental agents on the HTM aqueous flow facility.

Example 1

Human Trabecular Meshwork Cell Culture

1. Primary human trabecular meshwork (HTM) cells were purchased (from ScienCell Research Laboratories, Carlsbad, Calif.); or isolated from the juxtacanalicular and corneoscleral region of donor human eye tissue.

2. The HTM cells were plated in flasks, glass coverslips, and micropatterned 3-D micro- and nanostructured scaffolds coated with HTM biocompatible agents such as poly-L-lysine, gelatin etc., and cell proliferation compared; the HTM biocompatible coating which provided the optimal HTM cell proliferation was selected.

2.a. The HTM cells were plated in poly-L-lysine-coated 75 $cm^2$ cell culture flasks (2 μg poly-L-lysine/$cm^2$) and cultured in Improved MEM (Cellgro, Manassas, Va.) with 10% fetal bovine serum (ScienCell Research Laboratories, Carlsbad, Calif.). or 2.b. The HTM cells were plated in gelatin-coated (75 $cm^2$ cell culture flasks (1% sterile gelatin solution) and cultured in Improved MEM (Cellgro, Manassas, Va.) with 10% fetal bovine serum (ScienCell Research Laboratories, Carlsbad, Calif.).

3. Fresh culture medium was supplied every 48 hours.

4. Cells were maintained at 37° C. in a humidified atmosphere with 5% carbon dioxide until 80%-90% confluence.

5. Cells were trypsinized using 0.25% Trypsin/0.5 mM ethylenediaminetetraacetic acid (EDTA).

6. Then, subcultured.

7. After comparing the poly-L-lysine coating to gelatin for HTM cell attachment and growth, the HTM cells were sub cultured on gelatin-coated 75 $cm^2$ cell culture flasks. Gelatin-coating provided superior results than poly-L-lysine, but other HTM biocompatible coatings on the chosen micropatterned 3-D micro- and nanostructured scaffold may be tested with HTM cells and selected if superior desired cell attachment and proliferation results are observed.

8. All studies were conducted using cells before the 5th passage, for the HTM cells purchased herein. However, other choices of HTM cells may perform favorably under more passages.

Figure 5B:
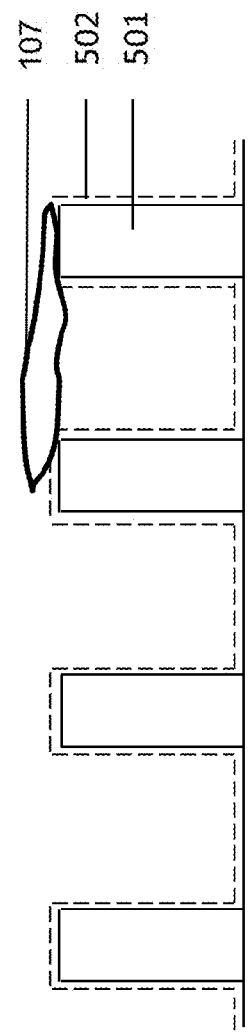
FIG. 5B is a schematic illustration of the development of a bioengineered human trabecular meshwork (HTM) in a sectional view of the HTM cells growing on a HTM biocompatible coated scaffold: Day>6; where 3-D micro and nanostructured scaffold 501; HTM biocompatible coating 502; TM cell 107.

Similar methods were used to derive the HTM cells used for cell seeding in FIG. 1; 109, and FIG. 5B. Choices of HTM cells may include epithelial cells, epidermal cells, endothelial cells, smooth muscle cells, stromal cells, neural cells, stem cells, but are not necessarily limited to the HTM cell types listed herein.

Example 2

3-D Micro- and Nanostructured Scaffold Fabrication

To produce the scaffolds with varying dimensions of micro- and/or nanostructures, using standard photolithography techniques shown in FIG. 4, a 3-D micro- and nanostructured scaffold with an architecture (FIG. 3A; 3B; 3C; 9) very similar to the specific features of the TM observed in vivo.

1. A silicon wafer (FIG. 4; 402) was cleaned using Piranha (3:1 $H_2SO_4$:$H_2O_2$).

2. Rinsed with deionized water.

3. Then dried with nitrogen.

4. A release layer (FIG. 4; 401) was then spun on the wafer at 3000 rpm using a spin coater. In this example, OMNIC-COAT™ treatment was used on previously cleaned silica wafer for the release layer (FIG. 4A; 401).

5. Baked on a hot plate at 200° C. for 1 min.

6. A substrate (in this example SU-8 2010) was applied by spin-coating to a final thickness of approximately 20 μm, (FIG. 4B; 403).

7. Then baked at 95° C. for 10 min.

8. Cooled to room temperature.

9. A resist is thus produced.

10. A micro- or nanostructure with desired pore size, beam width, beam height and other factors were selected for the mask (FIG. 4C; 404). The substrate was exposed through a mask containing the desired patterns (FIG. 4C).

11. A micro- and nanostructure was thus produced.

12. The micro- and nanostructure was baked at 95° C. for 10 min.

13. Cooled to room temperature.

14. Placed in propylene glycol methyl ether acetate (PG-MEA) developer overnight. The immersion of the micro- and nanostructure in PGMEA enabled the development and release of the 3-D micro- and nanostructured scaffolds from the wafer coated with release layer.

15. The released porous 3-D micro- and nanostructured scaffolds were then removed from the PGMEA solution (FIG. 4D).

16. The porous 3-D micro- and nanostructured scaffolds were created by cutting into disks that fit in a 24-well plate or microtiter plate for HTM cell growth, sterilized by soaking in 70% ethanol for 30 min, and reinforced by an autoclaved aluminum tape ring (FIG. 4E).

It will be understood that the invention has been described by way of example only and modifications may be made whilst remaining within the scope and spirit of the invention.

Example 3

Culture of HTM Cells on SU-8 Scaffolds

1. SU-8 3-D micro- and nanostructured scaffolds were coated by soaking for 30 minutes in a HTM biocompatible coating agent (for example poly-L-lysine or gelatin) to promote HTM cell attachment.

2. Coated SU-8 3-D micro- and nanostructured scaffolds were removed and allowed to air-dry overnight in a sterile environment like a sterile tissue culture hood.

3. SU-8 3-D micro- and nanostructured scaffolds were allowed to rest at the bottom of a 24-well plate while preventing direct contact between 3-D micro- and nanostructured scaffold and the bottom of the 24-well plate. For the present invention, a structure was designed and constructed for preventing direct contact between 3-D micro- and nanostructured scaffold and the bottom of a cell culture plate. Aluminum tape rings were cut, autoclaved and placed around the borders of the previously sterilized scaffolds. These tape rings allowed the 3-D micro- and nanostructured scaffolds to rest at the bottom of a culture plate while preventing direct contact between 3-D micro- and nanostructured scaffold and the bottom of the plates; This tape ring feature designed and constructed for the present invention also facilitates manipulation without handling cell-seeded scaffolds directly. However, differently designed and constructed structures may achieve the same desired features.

4. HTM cells were seeded on the HTM biocompatible coated SU-8 3-D micro- and nanostructured scaffolds at various cell densities (for example $1-2\times10^4$, $3-4\times10^4$ and $5-10\times10^4$ cells/well) (FIG. 11).

Figure 12:
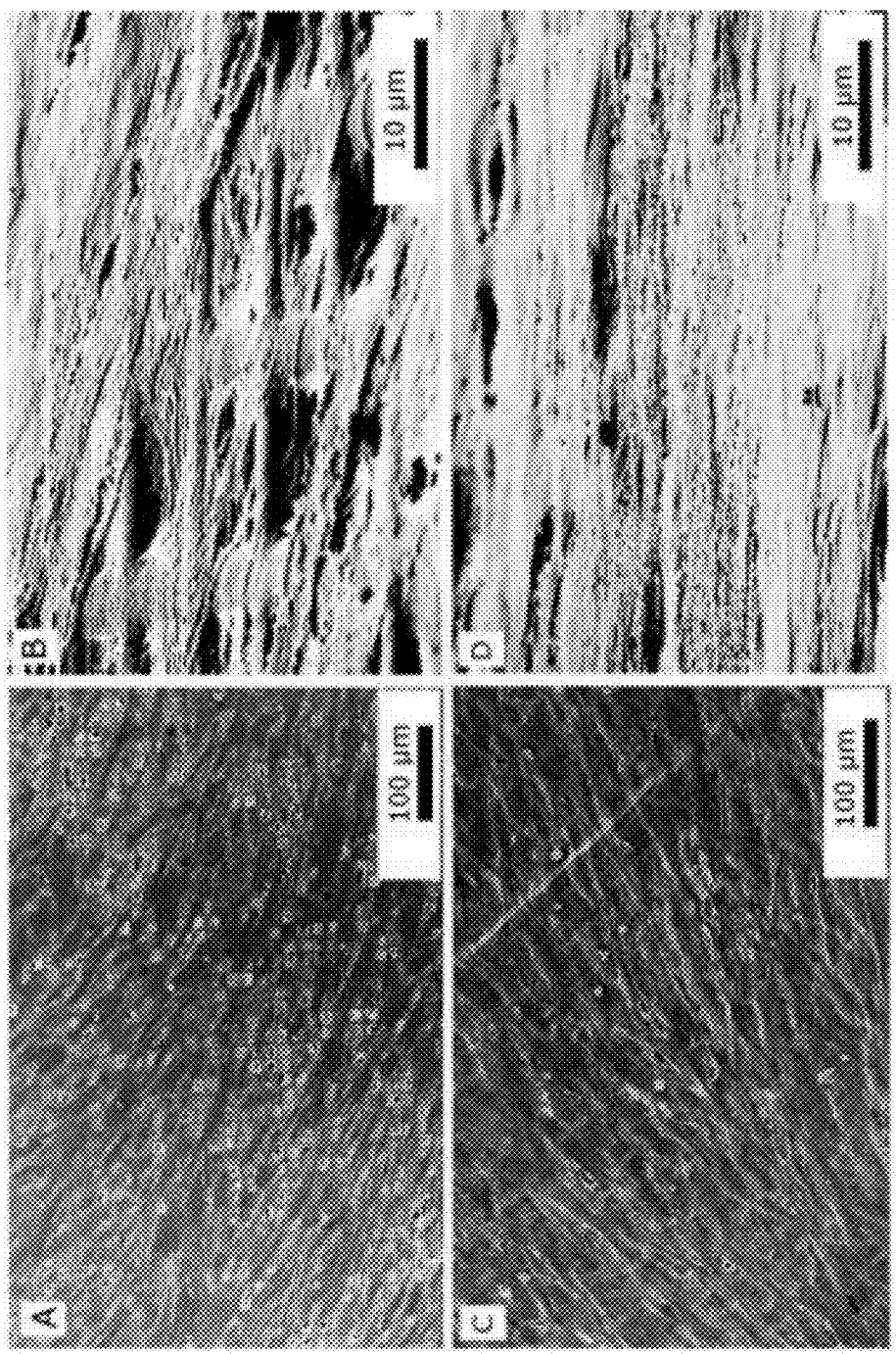
FIG. 12 is SEM micrographs of HTM cells grown on gelatin-coated SU-8 3-D micro- and nanostructured scaffolds with a pore size of 12 μm at 7 (A and B) and 14 (C and D) days after seeding.

5. Cell growth on the SU-8 3-D micro- and nanostructured scaffolds was monitored every 48 hours for 14 days (FIG. 12). A Nikon inverted TS-100 F microscope (Micro Video Instruments, Avon, Mass.) may be used.

Characterizing HTM and SC cell morphology using SEM, immunochemistry and confocal microscopy techniques, which are standard techniques well known to those of skill in the art (For HTM cells: Polansky et al., Ophthalmology. 1984 June; 91(6):580-95; For SC cells: Perkumas et al., Exp Eye Res. 2012 March; 96(1):82-7. doi: 10.1016/j.exer.2011.12.017. Epub 2011 Dec. 22).

Example 4

A Perfusion Chamber System using an Artificial Trabecular Meshwork (TM) in a High Throughput System setup within a Controlled Environment Using a "multi-channel Artificial TM Perfusion Array" (FIG. 2).

1. Set up a disposable cell-culture insert with a porous 3-D micro- and nanostructured scaffold, with or without a seeded cell culture (FIG. 2; 202).

2. Set up a re-usable or single-use effluent wells bottom structure (FIG. 2; 203).

3. Set up a re-usable fixed lid structure with desired number of fluidic inlets top structure (FIG. 2; 201).

4. Set up a Scaffold Holder construction comprising of at least a bottom structure, a top structure, a disposable cell-culture inserts, wherein connection to cell-culture inserts may be through O-ring compression seals (FIG. 2A-B).

5. Set up Pumps such as syringe pumps for introducing at least one media or media in combination with at least one experimental agent through multiple fluidic inlets (FIG. 2C; 204).

6. Set up Pressure transducers and flow monitors (FIG. 2C; 206).

7. Set up Temperature control monitors.

8. Set up a multi-channel artificial TM array monitoring system comprising of the scaffold holder construction connected through multiple channel inlets (FIG. 2C; 207) to at least the pumps such as syringe pumps, the pressure transducers, the flow monitors, and a temperature control monitor, in a housing maintaining a constant temperature (FIG. 2C).

Example 5

High Throughput Screening System

An example of a high throughput screening artificial TM system setup (FIG. 2c) may include the following in a system setup with a 6-channel perfusion array for artificial TM. The system would include a disposable cell-culture insert with SU-8 porous substrate (FIG. 2A; 202); a re-usable effluent wells (bottom) (FIG. 2A; 203) and fixed lid with fluidic inlets (top) (FIG. 2A; 201); connection to cell-culture inserts is through O-ring compression seals. The 6-channel artificial TM array would be supported within a housing comprising of a scaffold holder that is connected to pressure, flow (FIG. 2C; 206) and temperature instruments that would measure and monitor the flow rate, pressure and temperature of the fluids and effluents entering and exiting the perfusion array for artificial TM.

Example 6

An Artificial TM Device for Clinical Use

Figure 7:
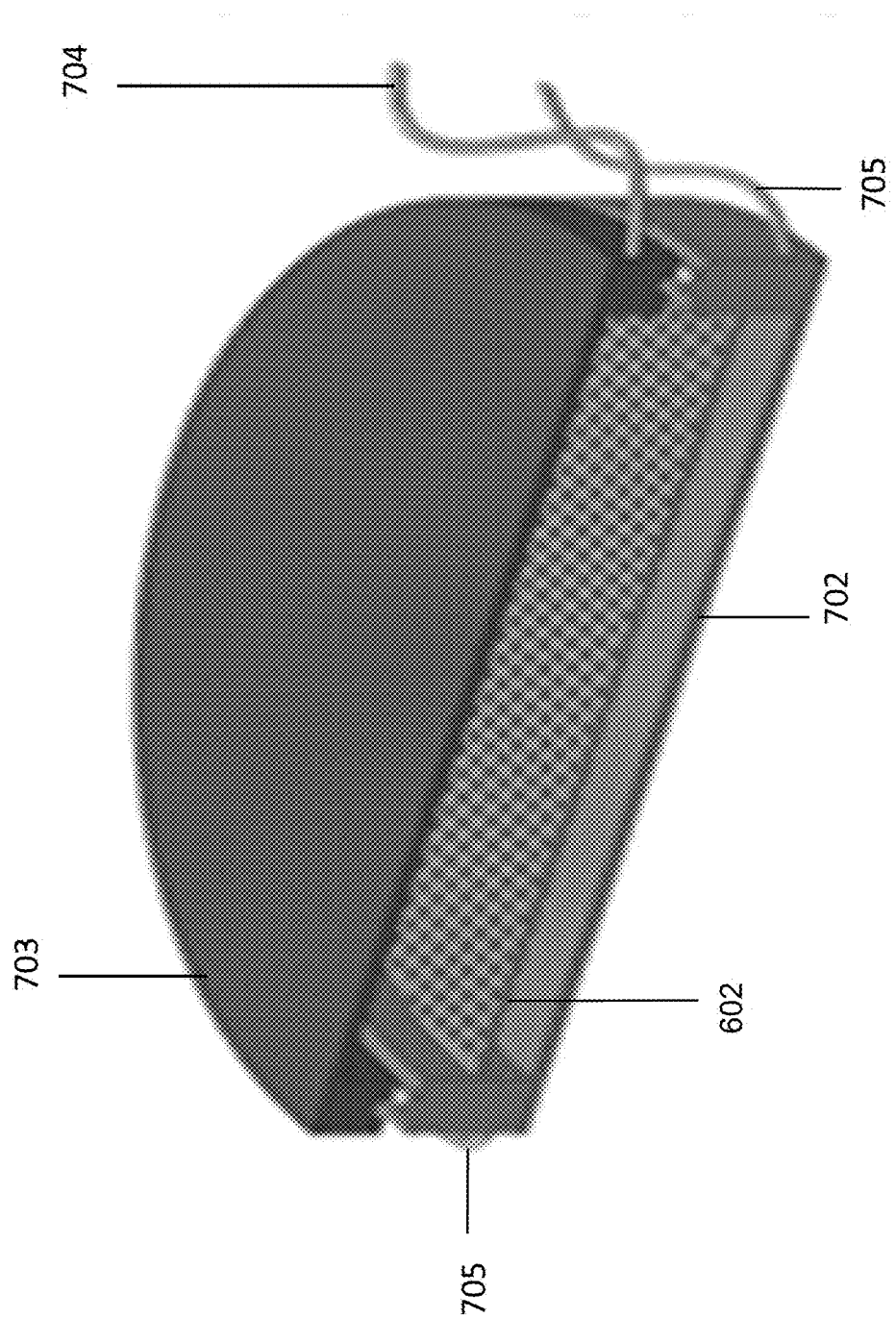
FIG. 7 is an artistic rendering of a bi-layered "artificial TM" used to treat IOP associated conditions, including glaucoma, in accordance with the present invention. 602 is the scaffold holder, 702 is the bottom cap, 703 is the upper lid, 704 is the inflow tubing, 705 is outflow tubing.

FIG. 6 showing a cross-sectional view of a human trabecular meshwork device derived from inventive concept herein. The human trabecular meshwork device as shown in FIG. 7 with cell support (FIG. 7) and bottom "cap" (FIG. 7; 702) in place. Upper lid is shown (FIG. 7, 703). One inlet and two outlet tubings are shown (FIG. 7; 704, 705). The thickness of the assembled device is designed to be between 0.7 and 2 mm and a perfusion area of approximately 115 $mm^2$.

The Ophthalmologist may perform a surgical incision at the limbus, raise the conjunctiva to expose the sclera and place the device on the sclera a few millimeters back from the limbus (typically 8-10 mm). The surgeon may then secure the device with non-absorbable sutures to the sclera to prevent movement. He will then insert the inflow tube through a limbal stab incision into the anterior chamber. He will then dissect above the Schlemm's canal to identify the canal. He will insert either a suture or a catheter into the canal and feed it into the canal until he reaches a point 180 degrees away. It is preferable to use a fiberoptic catheter for this maneuver as this allows constant feedback on the tip position. The surgeon would then inject viscoelastic material in the canal to facilitate insertion of the outflow tube. The maneuver will be repeated with the other outflow tube. Following insertion of the outflow tubes the surgeon will reinforce as needed the overlying tissues and will close the incision with sutures. Alternatively, the doctor may insert other configurations of the artificial TM inside the eye to replace the TM after it has been removed using methods known to those skilled in the art. Either way, the artificial TM device proposed here and shown in FIG. 7 may have potential as a routine first-line therapy for treatment of open-angle glaucoma and other types of glaucoma, even before eye drops are used but can also be used in conjunction with eye-drops.

Example 7

A High-Throughput Screening System for HTM Diseases Like Glaucoma

FIG. 1 is a process flow diagram that shows various iterations and variations in the work-flow to generate an artificial trabecular meshwork.

In this example, it is essential that the choice of cells could determine the resultant artificial HTM function, which can be measured in this invention concept. The 3-D micro- and nanostructured scaffold's pre-determined structure at micro- and/or nanoscale as per the concept of this invention would guide the seeded cells. The pore size and width of beams would be essential for an artificial trabecular meshwork to form. The present invention suggests the range.

Choices of source of cells are various including but not limited to cell lines, primary cells (FIG. 1; 104) isolated from eye tissues (FIG. 1; 100), cells derived from stem cells (FIG. 1; 106), bioengineered or genetically engineered cells (FIG. 1; 105). After harvesting, TM cells and/or SC cells (FIG. 1; 107, 108) will be seeded (FIG. 1; 109) onto 3-D micro- and nanostructured scaffolds (FIG. 1; 110) and cultured (FIG. 1; 111) to recreate artificial trabecular meshwork (FIG. 1; 112). The artificial TM will be incorporated into a flow chamber, an assembled micro-titer plate or a medical device, respectively, which can be used for understanding outflow physiology (FIG. 1; 113), high throughput therapeutics screening (FIG. 1; 114) and developing therapeutic devices (FIG. 1; 115). Follow up experiments might include small RNA interference studies of genetically modified cell source artificial HTM or studies of stem cell originated artificial HTM or studies of an artificial HTM originated from cells donated by individual patients.

For the purposes of success of this invention of an artificial HTM, cell characterization studies as follow up can show that the artificial HTM behaves like the natural HTM. Characterizing human trabecular meshwork (HTM) cell morphology (FIGS. 11-16) by (I) Using scanning electron microscopy (SEM) (FIGS. 11-12) and (II) Using immunocytochemistry and confocal imaging (FIGS. 13-14). See FIG. 16 for a glaucoma drug screening results through the artificial HTM.

Example 8

Bioengineering Pore Size (FIG. 3A; L1 &L2) and Beam Width and Height (FIG. 3B; H&W)

Figure 5C:
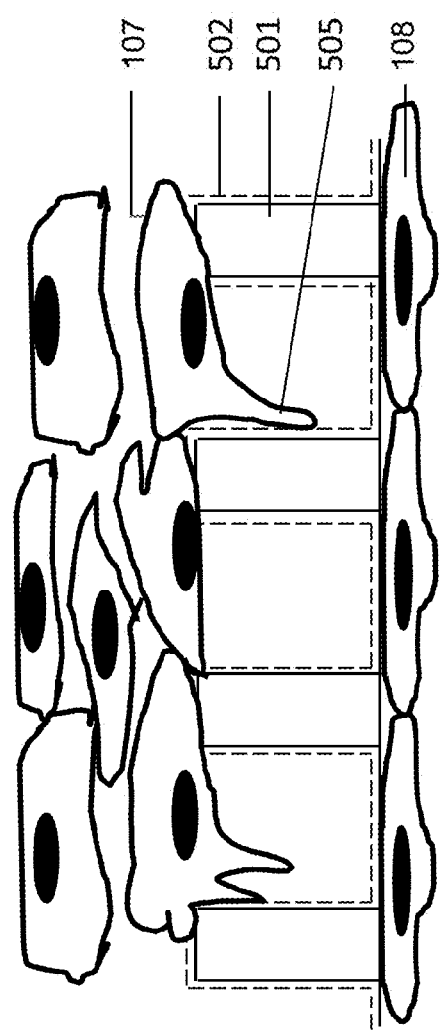
FIG. 5C is a schematic illustration of the development of a bioengineered human trabecular meshwork (HTM) in a sectional view of the HTM cells growing on a HTM biocompatible coated scaffold: HTM cell proliferation; where (1) 3-D micro and nanostructured scaffold 501; (2) HTM biocompatible coating 502; (3) TM cell 107; (4) SC cell 108.

As described herein, the present invention involves a bioengineered HTM construction to better recapitulate the perforated sheet-like structure and outflow characteristics of HTM. In one aspect of the invention, freestanding, microporous 3-D micro- and nanostructured scaffolds were fabricated containing an array of pores. In another embodiment, these scaffolds were fabricated containing beam widths and heights forming the walls of the pores, in which these beam widths and heights facilitated direction of the seeded HTM cells to send out cellular processes. FIG. 5C shows a cross-sectional illustrated view of such a beam height and width forming the walls of a pore, and providing a support element for a HTM cell process extension (FIG. 5C; 505). In one embodiment, the pore size ranges from 0.1 microns to 8 microns, 8 microns to 14 microns and 14 microns to 30 microns, and more preferably approximately 7, 12 and 15 µm and most preferably for HTM cell size of current invention approximately 10 microns to 12 microns (FIG. 3A: L1 & L2). In another embodiment for facilitating the formation of the three dimensional porous trabecular meshwork that mimics the in vivo TM with beam widths approximately ranging from 0.1 microns to 20 microns and more preferably approximately 3.4±0.1 µm, 7.3±0.1 µm and 5.2±0.1 µm ($p<0.05$) (FIG. 3B: W&H), respectively. We chose these pore sizes for this invention because they are close to the size of a single HTM cells of our present invention's cell source. One preferred embodiment is that the pore size selected to fabricate the 3-D micro- and nanostructured scaffold, are smaller than the size of the HTM cell size selected to seed the 3-D micro- and nanostructured scaffold, since a preliminary study in this invention showed it was difficult for HTM cells to grow into a confluent layer on microstructures with pore size larger than that of the cell since cells were unable to expand over or fully populate the pores (data not shown). In another preferred embodiment, the pore size, width and height (FIGS. 3A; L1 &L2 and 3B; H&W) respectively, conferred the ability on the select HTM seeded cells to form cell processes capable of interacting with neighboring cell processes and forming a three-dimensional porous meshwork of at least a single layer of HTM cells with an approximate thickness of 20 microns. It will be appreciated from the results of this invention to those of skill of the art that should the HTM cell source and their resultant cell sizes be slightly different from the current HTM cell size the preferred pore size and beam and width dimension might be slightly different.

Example 9

Construction of a Scaffold Holder

In one aspect of the invention, a scaffold holder was constructed comprising of a housing wherein there is a first element including a microtiter plate designed as an insert to hold the 3-D micro- and nanostructured scaffolds (FIG. 2A; 202); a second element including a bottom array designed to collect effluents (FIG. 2A; 203); and a third element including a top plate designed to allow entry of perfusion media in a sealed manner (FIG. 2A; 201). For the present invention, in a preferred embodiment, this scaffold holder is set up to hold a microtiter multi-well plate for high-throughput screening format.

In yet further aspects of the present invention, such a scaffold holder in a perfusion chamber maintained at a constant temperature and flow rate, will have the ability to maintain a constant flow rate for HTM cells at 0.1-15 µl/min and 15-30 µl/min and 30-60 µl/min or more than 60 µl/min to study the effect on the HTM in the present invention during screening.

In another aspect of the present invention, this scaffold holder is located within a sealed perfusion chamber providing a tool for studying in a controlled environment for temperature and pressure flows (FIG. 2C; 206) the HTM set up in the scaffold holder arrays. In yet another aspect of this invention, this scaffold holder is connected to a pressure transducer within a perfusion chamber, allowing for flow and measurements of a constant flow rate of perfusion media, in a controlled temperature, through the 3-D micro- and nanopatterned scaffolds with or without HTM cellular cultures. Those of skill of the art will appreciate the numerous parameters such a construction provide for a controlled environment and pressure flow rate to demonstrate how closely the HTM 3-D micro- and nanostructured scaffold mimics an in vivo HTM and allows for screening studies and therapy comparisons.

Example 10

Construction of a Bilayered TM

The final product may be a two-component system. A fixed component which will involve the pumping and sensing mechanisms and a disposable component which will include the carrier on which the HTM cells and SC cells grow and are then perfused. Because of the common practice of using multi-well plates in cell culture, we will design the disposable porous substrate component to fit in off-the-shelf 24-well plates. This will greatly simplify the phase of growing HTM cells prior to using them for flow facility measurement experiments.

The carrier containing confluent HTM cells will then be placed in a non-disposable re-sterilizable 6-well chamber (FIG. 2C; 207). The connection to the pumping system and pressure sensor package (FIG. 2C; 204, 206) will be through an O-ring compression seal. Medium will be injected into each of the wells using 2 programmable multi-channel pumps. Each pump will be used to control flow in 3 wells so that experiments can be run in triplicate to ensure validity of the results. An additional pair of programmable pumps will connect to the system to allow injection of medium containing pharmaceutical agent of interest at the appropriate concentration.

Perfusion will be performed at a constant flow rate that will be feedback-controlled using pressure data. Initially through flow will be adjusted to obtain an average pressure of ~5 mmHg in each three-well group controlled by one pump (FIG. 2C; 204). Individual pressure sensors for each well will ensure that excessively low or high pressures caused by accidental leakage or air obstruction respectively can be detected. After the system stabilizes for at least 2 hours, medium containing the agent of choice can be injected in the wells using the second set of pumps (FIG. 2C; 204). Again flow will be adjusted to maintain an average IOP 5 mmHg and the system allowed to reach steady-state. At that point flow will be increased to obtain an average IOP of approximately 15 mmHg and after reaching steady state again flow rates will be recorded. The difference in flow rates divided by the pressure in each well will be used to calculate flow facility in each individual well. Flow with basic media will allow washout of the agent and test reversibility of effect.

Example 11

A Design, Construction and Characterization of an Artificial Human Trabecular Meshwork (HTM)

IA Materials

All chemicals were purchased from Sigma-Aldrich unless otherwise specified.

IB Human Trabecular Meshwork Cell Culture

Primary HTM cells, isolated from the juxtacanalicular and corneoscleral region of human eye, were purchased from ScienCell Research Laboratories (Carlsbad, Calif.). The HTM cells were initially plated in poly-L-lysine-coated 75 cm$^2$ cell culture flasks (2 µg poly-L-lysine/cm 2) and cultured in Improved MEM (Cellgro, Manassas, Va.) with 10% fetal bovine serum (ScienCell Research Laboratories, Carlsbad, Calif.). Fresh culture medium was supplied every 48 hours. Cells were maintained at 37° C. in a humidified atmosphere with 5% carbon dioxide until 80%-90% confluence at which point cells were trypsinized using 0.25% Trypsin/0.5 mM EDTA and subcultured. After comparing the poly-L-lysine coating to gelatin for HTM cell growth, the following HTM cells were subcultured on gelatin-coated 75 cm$^2$ cell culture flasks. All studies were conducted using cells before the 5th passage.

IC. SU-8 3-D Micro- and Nanostructured Scaffold Fabrication

SU-8 2010 (MicroChem Corp., Newton, Mass.) was used to develop free-standing porous microstructures that served as 3-D micro- and nanostructured scaffolds for HTM cell culture. SU-8 3-D micro- and nanostructured scaffolds with varying dimensions of microstructures were fabricated using standard photolithography techniques (FIG. 4). First, a silicon wafer was cleaned using Piranha (3:1 $H_2SO_4$:$H_2O_2$) ($H_2SO_4$ was purchased from Transene Company, Danvers, Mass. and $H_2O_2$ from Puritian Products, Bethlehem, Pa.), rinsed with deionized water and then dried with nitrogen. A release layer of Omnicoat (Microchem, Boston, Mass.) was then spun on the wafer at 3000 rpm using a spin coater (Brewer Science, Rolla, Mo.), and baked on a hot plate at 200° C. for 1 min. SU-8 2010 (Microchem) was applied by spin-coating to a final thickness of approximately 20 µm, then baked at 95° C. for 10 min, and cooled to room temperature. The resist was exposed through a mask containing the desired patterns using a 150 mJ/cm$^2$ dose on an EVG 640 1-line Contact Aligner (EV Group, Albany, N.Y.). Finally, the substrate was baked at 95° C. for 10 min, cooled to room temperature and placed in PGMEA developer (Microchem) overnight. The immersion of the substrate in PGMEA enabled the development and release of the SU-8 3-D micro- and nanostructured scaffolds. The released SU-8 porous scaffolds were then removed from the PGMEA solution and sterilized by soaking in 70% ethanol for 30 min.

ID. Culture of HTM Cells on SU-8 Scaffolds

SU-8 3-D micro- and nanostructured scaffolds were coated with poly-L-lysine or gelatin to promote HTM cell attachment. by soaking in 10 mg/mL poly-L-lysine or 1% sterile gelatin solution for 30 min, after which these HTM biocompatible coated scaffolds were removed and allowed to air-dry in a sterile tissue culture hood overnight. Aluminum tape rings were cut, autoclaved and placed around the borders of these previously sterilized HTM scaffolds. This allows these sterilized, HTM biocompatible coated, SU-8 3-D micro- and nanostructured scaffolds to rest at the bottom of a 24-well plate while preventing direct contact between these scaffolds and the bottom of the plate; the ring also facilitates manipulation without handling cell-seeded scaffolds directly. HTM cells were seeded on these scaffolds at various cell densities ($1 \times 10^4$, $2 \times 10^4$, $4 \times 10^4$ and $5 \times 10^4$ cells/cm$^2$). Cell growth was monitored by a Nikon inverted TS-100 F microscope (Micro Video Instruments, Avon, Mass.) every 48 hours for 14 days.

Cells were characterized using standard procedures for SEM, Immunocytochemistry and confocal imaging, well known to those of skill in the art.

IE. Perfusion Studies

A flow system apparatus for the controlled flow pressure measurement was constructed as shown in FIG. 2C was contained in a perfusion chamber housing comprised of at least a perfusion chamber with an integrated pressure transducer (FIG. 2C; 206), the sterilized, HTM biocompatible coated, SU-8 3-D micro- and nanostructured scaffold with or without HTM cells placed within a cell-culture insert (FIG. 2A; 202) and were secured in the scaffold holder, comprising at least a bottom element adapted for effluent (FIG. 2A; 203), a top element adapted for media entry (FIG. 2A; 201) inside the perfusion chamber (FIG. 2c). This flow system allowed for simultaneous control of the flow and measurement of the transmembrane pressure, permitting the exploration of the outflow characteristics of the in vitro HTM model. Fourteen days prior to perfusion measurements, $4 \times 10^5$ cell/cm$^2$ HTM cells were seeded on these sterilized, HTM biocompatible coated, SU-8 3-D micro and nanostructured scaffolds. At day 14, samples were placed in the perfusion chamber (FIG. 2C; 207) and were perfused at 2, 10 and 40 μm/min in the apical-to-basal direction for 24 hrs, respectively, with perfusion media comprising Dulbecco's modified Eagle's medium (DMEM) containing 0.1% gentamicin. The temperature was kept constant at 34° C. within the perfusion chamber housing (FIG. 2C; 207). Back pressures were continuously monitored with a pressure transducer (FIG. 2C; 206) and recorded. For the treatment with Lat-B, once a stable baseline pressure was reached through perfusion of media and HBSS as described above, samples were then perfused with 20 μM Lat-B in Hank's balance salt solution (HBSS) at the same constant flow and temperature for 4 hrs. Samples were fixed and stained for SEM and confocal image analysis as described above.

II. Results

IIA. Design and Evaluation of SU-8 Scaffold-Based HTM Culture System

To better recapitulate the perforated sheet-like structure and outflow characteristics of HTM, we fabricated free-standing, microporous membranes of SU-8 3-D micro- and nanostructured scaffolds. These scaffolds contain arrays of square pores 7, 12 and 15 μm (FIG. 3A; L1 &L2), with beam widths of 3.4±0.1 μm, 7.3±0.1 μm and 5.2±0.1 μm (FIGS. 3B; W), respectively. We chose these pore sizes because they are close to the size of a single HTM cells. Our preliminary study showed that it was difficult for HTM cells to grow into a confluent layer on microstructures to with pore size larger than that of the cell since cells were unable to expand over or fully populate the pores (data not shown). The thickness of these free-standing 3-D micro- and nanostructured scaffolds was measured to be 20 μm through SEM analysis.

SEM and light microscopy were used to evaluate the effects of biomacromolecular HTM biocompatible coating, initial cell seeding density, pore size of 3-D micro- and nanostructured scaffold, and culture period on HTM cell attachment and growth on these scaffolds. To recapitulate the functional morphology of HTM, we expected the sterilized, HTM biocompatible coated, SU-8 3-D micro- and nanostructured scaffold-based culture system to provide the most cell coverage, enhancing HTM cell growth to form confluent perforated meshwork with laminar layers.

Initial screening of HTM biocompatible coating factors (gelatin vs. poly-L-lysine) demonstrated that 3-D micro- and nanopatterned SU-8 scaffolds coated with gelatin showed greater cell attachment and higher percentage of confluence after culturing for 10 days, and thus all scaffolds used in our work were HTM biocompatible coated with 1% gelatin prior to cell seeding. The effect of initial cell seeding density ($1\times10^4$, $2\times10^4$, $4\times10^4$ and $5\times10^4$ cells/cm$^2$) on HTM cell attachment and growth on all SU-8 scaffolds was evaluated through SEM observation. When the cell seeding density was lower than $4\times10^4$ cells/cm$^2$, it exhibited poor cell attachment and low cell growth. The results demonstrated that $4\times10^4$ cells/cm$^2$ was the lowest initial cell seeding density that allowed confluent cell layer formation. The cell seeding density greater than $4\times10^4$ cells/cm$^2$ showed no improvement in cell layer formation (data not shown). Therefore $4\times10^4$ cells/cm$^2$ seeding density was used for construction of the in vitro HTM model.

The effect of pore size (7, 12 and 15 μm) (FIG. 3A; L1 & L2) of SU-8 scaffolds on HTM cell growth was compared. By day 7, cells grown on the 7 μm SU-8 scaffolds exhibited less cell coverage (FIG. 11D). HTM cells grown on 12-μm SU-8 scaffolds fully covered the pore spaces (FIG. 11E) and began secreting their fibrillar, mesh-like extra-cellular matrix (ECM) evenly throughout the scaffold and between the cells. Cells grown on 15 μm SU-8 scaffolds showed larger non-cell covered areas (FIG. 11F). The effect of pore size on HTM cell attachment and growth was even more pronounced at the low cell density ($1\times10^4$ cells/cm$^2$) where the 12-μm SU-scaffold provides the best cell coverage among all three pore sizes (compared in FIGS. 11A-F). Additionally, observation under light microscopy showed that fewer cells attached to these two scaffolds compared to the 12-μm SU-8 scaffolds (data not shown).

The effect of culture period of HTM cell growth on 12-μm SU-8 scaffolds was further evaluated. Compared to 7 days of cultivation, cells grown for 14 days achieved full coverage (FIG. 12). In order to further assess whether the extended culture period could enhance cell layer formation, HTM cells on SU-8 scaffolds were allowed to grown for 21 days. No apparent difference was noted through SEM and light microscopy observation (data not shown). Additionally, HTM cells grown on the 12-μm SU-8 3-D micro- and nanostructured scaffolds exhibited a spindle-shaped appearance, representative characteristics of HTM cells, while presenting characteristic microvillus projections and overlapping cell processes. The results demonstrated that, sterilized, gelatin-HTM biocompatible coated, 12-μm SU-8 micro- and nanostructured scaffolds could provide the most favorable scaffolds, enhancing HTM cell growth and confluent meshwork formation (FIGS. 11-14).

IIB. Biological Characterization of Bioengineered HTM

After we demonstrated the feasibility of constructing an in vitro HTM model system by culturing $4\times10^4$ cells/cm$^2$ cells on sterilized, gelatin-HTM biocompatible coated 12-μm SU-8 3-D micro- and nanostructured scaffolds for 14 days, we confirmed HTM-specific gene expression in the bioengineered HTM using immunocytochemistry analysis followed by confocal imaging. Confocal images showed that these HTM cells grown on SU-8 scaffolds expressed α-SMA (FIG. 13A), myocilin and αB-crystallin (FIG. 13B), suggesting that these cells maintained an HTM-like expression pattern. Additionally, F-actin staining characterized the cytoskeleton as containing partially elongated stress fibers, which also appeared to be aligned. Three-dimensional confocal reconstruction by z-stacking of F-actin demonstrated that HTM cells grew on top of the SU-8 3-D micro- and nanostructured scaffolds as dense multilayers, forming a 3-D meshwork approximately 20 μm thick (FIGS. 14B-C). Additionally, cells that constitute the primary (basal) layer sent thin fibrous processes into these SU-8 micro- and nanostructured scaffolds (FIGS. 14B-C; 301).

IIC. Functional Analysis of Bioengineered HTM

The fact that HTM cells grown on gelatin-coated 12 μm SU-8 scaffolds maintained HTM cell phenotype promoted us to further evaluate the outflow facility of the bioengineered HTM using a flow system apparatus as shown in FIG. 2. The construct of HTM cells cultured on these HTM biocompatible coated, SU-8 3-D micro- and nanostructured scaffolds for 14 days was incorporated into a stand-alone perfusion chamber, where the pressure across the tissue construct was measured using an integrated pressure sensing system while maintaining a constant flow rate (40 μl/min). HTM cells provided flow resistance, raising the transmembrane pressure to 8±1 mmHg, while SU-8 scaffolds alone (without HTM cells) had no significant resistance to flow (transmembrane pressure of 0.3±0.5 mm Hg). Pressure measurements at different flow rates (2, 10 and 40 μl/min) allowed for calculation of the outflow facility of the bioengineered HTM. Transmembrane pressure (P) was plotted as a function of flow rate (F) and the linear regression gave rise the slope which was the value of change of transmembrane pressure (ΔP)/the change of flow rate (ΔF) (FIG. 8). Since the outflow facility could be determined by ΔF/ΔP, the outflow facility was given by the inverse of the slope, and was found to be 4.7 µl/min/mmHg (4.2-5.1 µl/min/mmHg with 95% confidence).

IID. Physiological Response of Bioengineered 3-D HTM to Latruncunlin B

To further verify that our system allows HTM cells to behave in a "physiological manner", Lat-B was added to the perfusate at a concentration of 2 µM for 4 hours. The mechanism of action of Lat B is reversible disruption of the dynamic process of actin filament maintenance, which affects the cytoskeleton of cells through net actin depolymerization. This agent decreased the resistance to flow by 92±6% (FIG. 16, N=8, p<0.05). Furthermore, Lat-B appeared to increase the outflow facility of our system by inducing shrinkage of HTM cells and disruption of secreted ECM. SEM images (FIGS. 15A-F) showed that HTM cells changed their morphology dramatically from elongated spindle-shape appearance to square-like shape after Lat-B treatment (FIG. 15C). Additionally, thick fibrillose bundles of circular appearance were seen throughout the entire scaffold under SEM. Confocal images showed that elongated actin fibers were disturbed and became punctate actin bundles after Lat-B perfusion, suggesting the critical role of actin filaments in maintaining HTM morphology and outflow physiology. Confocal z-stack analysis revealed that after Lat-B treatment the 3-D structure of the bioengineered HTM collapsed, with many cells falling into the pores of the scaffold.

III. Feasibility and Utility of this Invention

In this study, the feasibility of using HTM biocompatible coated, porous SU-8 3-D micro- and nanopatterned scaffolds to coax HTM cells into functional trabecular meshwork has been demonstrated herein (FIGS. 9-16). An in vitro HTM model system has been constructed in this invention. It includes the biomacromolecule HTM compatible coated SU-8 3-D micro- and nanopatterned scaffold for HTM cells growing into a confluent meshwork-like construct and a perfusion chamber with an integrated pressure transducer for sensing the transmembrane pressure under constant flow.

It offers a new avenue for understanding the HTM physiology at molecular and cellular level; testing pharmacological agents that affect IOP and trabecular outflow facility in humans; and contributes to the 3-D micro- and nanopatterned design and construction of a medical device comprising of therapeutic inserts to manipulate IOP by repairing a defective trabecular outflow facility.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components, the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application. Further, where a component, step, or feature is described singularly using "a" or "an", etc., there may be one or more of such component (plurality), steps or features included within the scope of the invention.

REFERENCES

[1] Tamm, E. R., The trabecular meshwork outflow pathways: structural and functional aspects. Exp Eye Res, 2009. 88(4): p. 648-55.
[2] Tektas, O. Y. and E. Lutjen-Drecoll, Structural changes of the trabecular meshwork in different kinds of glaucoma. Exp Eye Res, 2009. 88(4): p. 769-75.
[3] Overby, D. R., W. D. Stamer, and M. Johnson, The changing paradigm of outflow resistance generation: towards synergistic models of the JCT and inner wall endothelium. Exp Eye Res, 2009. 88(4): p. 656-70.
[4] Johnson, M., 'What controls aqueous humour outflow resistance?'. Exp Eye Res, 2006. 82(4): p. 545-57.
[5] Heijil A., Leske M. G., Bengtsson B., Hyman L., Hussein M. Reduction of intraocular pressure and glaucoma progression: results from the early manifest glaucoma trial. Arch Ophthalmol, 2002. 120(10):1268-79
[6] Peterson, J. A., et al., Effect of latrunculin-B on outflow facility in monkeys. Exp Eye Res, 2000. 70(3): p. 307-13.
[7] Ethier C. R., A. T. Read, and D. W. Chan, Effects of latrunculin-B on outflow facility and trabecular meshwork structure in human eyes. Invest Ophthalmol Vis Sci, 2006. 47(5): p. 1991-8.
[8] Tian B., Geiger B., Epstein D. L., Kaufman P. L. Cytoskeletal involvement in the regulation of aqueous humor outflow. Invest Ophthalmol Vis Sci, 2000. 41(3): p. 619-23.
[9] Spector I., Shochet N. R., Kashman Y., Groweiss A. Latrunculins: novel marine toxins that disrupt microfilament organization in culture cells. Science, 1983; 216 (4584): 493-5
[10] McKee, C. T., et al., The effect of biophysical attributes of the ocular trabecular meshwork associated with glaucoma on the cell response to therapeutic agents. Biomaterials, 2011. 32(9): p. 2417-23.
[11] Vaajanen, A., H. Vapaatalo, and O. Oksala. A modified in vitro method for aqueous humor outflow studies in enucleated porcine eyes. J Ocul Pharmacol Ther, 2007. 23(2): p. 124-31.
[12] Russell, P., et al. Response of Human Trabecular Meshwork Cells to Topographic Cues on the Nanoscale Level. Invest Ophthalmol Vis Sci, 2008. 49(2): p. 629-635.
[13] Schlunck, G., et al., Substrate rigidity modulates cell matrix interactions and protein expression in human trabecular meshwork cells. Invest Ophthalmol Vis Sci, 2008. 49(1): p. 262-9.
[14] Fautsch, M. P., et al., Primary trabecular meshwork cells incubated in human aqueous humor differ from cells incubated in serum supplements. Invest Ophthalmol Vis Sci 2005. 46(8): p. 2848-56.
[15] Koga, T., et al., Rho-associated protein kinase inhibitor, Y-27632, induces alterations in adhesion, contraction and motility in cultured human trabecular meshwork cells. Exp Eye Res, 2006. 82(3): p. 362-70.
[16] Bahler, C. K., et al., Prostaglandins increase trabecular meshwork outflow facility in cultured human anterior segments. Am J Ophthalmol, 2008. 145(1): p. 114-9.
[17] Bahler, C. K., et al., Trabecular bypass stents decrease intraocular pressure in cultured human anterior segments. Am J Ophthalmol, 2004. 138(6): p. 988-94. [18] Bogdanov, A. L. and Peredkov, S. S., Use of SU-8 photoresist for very high aspect ratio x-ray lithography. Microelectronic Engineering, 2000; 53: 493-496.
[19] Liu, C., Recent developments in polymerMEMS. Adv Mater, 2007; 19: 3783-3790.
[20] Mata A., Fleischman A. J., Roy S., Fabrication of multi-layer SU-8 microstructure. J. Micromech. Microeng. 2006; 16:276-84
[21] Mataa A., Kima E. J., Boehma C. A., Fleischmana A. J., Muschlera G. F., Roya S. A three-dimensional scaffold with precise micro-architecture and surface micro-textures. Biomaterials, 2009. 30(27): p. 4610-17
[22] Perkin T. W., Alvarado J. A., Polansky J. R., Stilwell L., Maglio M. and Juster R. Trabecular meshwork cells grown on filters. Invest Ophthalmol Vis Sci, 1988. 29(12): 1836-1846
[23] Freddo T. F., Patterson M. M., Scott D. R., and Epstein D. L. Influence of mercurial sulfhydryl agents on aqueous outflow pathways in enucleated eyes. Invest Ophthalmol Vis Sci, 1984. 25:278-285
[24] W. H. Spencer, J. Alvarado, and T. L. Hayes. Scanning electron microscopy of human ocular tissues: trabecular meshwork. Invest Ophthalmol Vis Sci, 1968. 7(6):651-662
[25] Johnson, D. H. Trabecular meshwork and uveoscleral outflow models. J Glaucoma 2005; 14:308-310
[26] Clayton T. McKee, Joshua A. Wood, Nihar M. Shah, Marion E. Fischer, Christopher M. Reilly, Christopher J. Murphy, Paul Russell, The effect of biophysical attributes of the ocular trabecular meshwork associated with glaucoma on the cell response to therapeutic agents. Biomaterials, 2011. 32(9):2417-2423.
[27] Sara M. Thomasy, Joshua A. Wood, Philip H. Kass, Christopher J. Murphy, Paul Russell. Substratum Stiffness and Latrunculin B Regulate Matrix Gene and Protein Expression in Human Trabecular Meshwork Cells. Invest Ophthalmol Vis Sci. 2012. 53(2): 952-958.
[28] Julie A. Last, Tingrui Pan, Yuzhe Ding, Christopher M. Reilly, Kate Keller, Ted S. Acott, Michael P. Fautsch, Christopher J. Murphy, Paul Russell. Elastic Modulus Determination of Normal and Glaucomatous Human Trabecular Meshwork. Invest Ophthalmol Vis Sci. 2011 April; 52(5): 2147-2152.
[29] Joshua A. Wood, Clayton T. McKee, Sara M. Thomasy, Marion E. Fischer, Nihar M. Shah, Christopher J. Murphy, Paul Russell. Substratum Compliance Regulates Human Trabecular Meshwork Cell Behaviors and Response to Latrunculin B Invest Ophthalmol Vis Sci. 2011. 52(13): 9298-9303.

We claim:

1. A method for forming an artificial eye outflow system comprising the steps of:
(a) providing a wafer with an upper surface;
(b) applying a release layer to the upper surface of the wafer, thereby yielding a top surface;
(c) layering a substrate on the top surface;
(d) constructing a microstructured or nanostructured three-dimensional (3-D) SU-8 scaffold from the substrate, the 3-D SU-8 scaffold comprising a microstructured or nanostructured plurality of pores forming a patterned, porous grid structure having a porosity of greater than 20%, each pore of the plurality having:
a uniform pore size, wherein the uniform pore size is a size within a range, wherein the range is greater than 7 μm to 15 μm,
a first measurement (L1) and a second measurement (L2), both the first measurement (L1) and the second measurement (L2) of a size to prevent growth of trabecular network (TM) cells or Schlemm's canal (SC) cells within the pore, and
a set of four walls defining a 3-D pore shape, the set of four walls having a beam width (W) and a beam height (H),
wherein the constructing comprises using a mask to define the 3-D pore shape of each pore of the plurality to set a predetermined pore size and beam width size;
(e) releasing the 3-D SU-8 scaffold from the top surface;
(f) sterilizing the 3-D SU-8 scaffold;
(g) coating the 3-D SU-8 scaffold with a biocompatible coating to produce a coated 3-D SU-8 scaffold, wherein the biocompatible coating provides attachment for TM cells and/or SC cells;
(h) seeding the coated 3-D SU-8 scaffold with TM cells and/or SC cells at a pre-determined cell seeding density; and
(i) culturing the cells on the coated 3-D SU-8 scaffold for a period of time sufficient for the formation of a confluent monolayer on the surface of the coated 3-D SU-8 scaffold, such that an artificial trabecular meshwork is formed that mimics the perforated sheet-like structure, outflow facility, and physiological function of an in vivo trabecular meshwork.

2. The method for forming an artificial eye outflow system of claim 1, further comprising the step of:
assessing cell morphology of the TM cells or SC cells.

3. The method for forming an artificial eye outflow system of claim 1, wherein the beam width (W) is from about 0.1 μm to about 20 μm.

4. The method for forming an artificial eye outflow system of claim 3, wherein the beam height (H) is from about 0.1 μm to about 20 μm.

5. The method for forming an artificial eye outflow system of claim 1, wherein trabecular meshwork cells are cultured on a first side of the 3-D SU-8 scaffold and wherein Schlemm's canal cells are cultured on a second side of the 3-D SU-8 scaffold.

6. The method for forming an artificial eye outflow system of claim 5, wherein the second side of the 3-D SU-8 scaffold is opposite the first side of the 3-D SU-8 scaffold.

7. The method of claim 1, wherein the microstructured or nanostructured 3-D SU-8 scaffold is not in direct contact with the bottom of a cell culture plate.

8. The method of claim 1, wherein the uniform pore size is 10-12 μm.

9. An artificial eye outflow system comprising:
a micro- and/or nanofabricated 3-dimensional (3-D) SU-8 scaffold, the 3-D SU-8 scaffold comprising a microstructured or nanostructured plurality of pores forming a patterned, porous grid structure having a porosity of greater than 20%, each pore of the plurality having:
a uniform pore size, wherein the uniform pore size is a size within a range, wherein the range is greater than 7 μm to 15 μm,
a first measurement (L1) and a second measurement (L2), both the first measurement (L1) and the second measurement (L2) of a size to prevent growth of trabecular meshwork (TM) or Schlemm's canal (SC) cells within the pore, and
a set of four walls defining a 3-D pore shape, the set of four walls having a beam width (W) and a beam height (H); and
wherein the 3-D SU-8 scaffold is covered with a confluent monolayer of TM cells or SC cells, such that the system mimics the perforated sheet-like structure, outflow facility, and physiological function of an in vivo trabecular meshwork.

10. The artificial eye outflow system of claim 9, wherein the uniform pore size is 10-12 μm.

11. An in vitro system for high-throughput screening in a multi-well plate of pharmacological agents affecting intraocular pressure and trabecular outflow comprising:
(a) the artificial eye outflow system of claim 9;
(b) a perfusion chamber comprising a housing with a controlled environment chamber maintained at a constant temperature and flow rate; and
(c) a multi-channel perfusion array comprising:
a first element, wherein the first element comprises a multi-well plate insert, wherein the multi-well plate insert holds the artificial eye outflow system;
a second element comprising a bottom multi-well plate, wherein the bottom multi-well plate is an effluent collector;
a third element comprising a top multi-well plate, and a perfusion media inlet fluidly connected to the top multi-well plate, and wherein the first element is sandwiched between the second element and the third element; and
a fourth element, wherein the fourth element comprises an artificial eye outflow system holder wherein the artificial eye outflow system holder;
separates the first element from the artificial eye outflow system, and
prevents the artificial eye outflow system from touching the bottom multi-well plate.

12. The in vitro system of claim 11 further comprising:
a pressure transducer.

13. The in vitro system of claim 12 wherein the pressure transducer maintains a constant flow rate at about 0.1 μl/min to about 60 μl/min.

14. The in vitro system of claim 11 comprising:
a pressure transducer having the ability to maintain a constant flow rate for trabecular meshwork cells at about 30 μl/min to about from 60 μl/min.

15. A method for high-throughput screening of an agent that modulates eye outflow comprising the steps of:
(a) providing the in vitro system of claim 11; and
(b) flowing media or fluid through the in vitro system, wherein the media or fluid comprises a test agent.

16. The in vitro system of claim 12, wherein the pressure transducer is functionally connected to the scaffold holder.

17. The in vitro system of claim 16, further comprising:
a monitor functionally connected to the pressure transducer.

18. The in vitro system of claim 16, further comprising:
a perfusion media entry system functionally connected to the pressure transducer.

19. The in vitro system of claim 16, further comprising:
an experimental agent media entry system functionally connected to the pressure transducer.

* * * * *